US009913487B2

(12) United States Patent
Luethy et al.

(10) Patent No.: US 9,913,487 B2
(45) Date of Patent: *Mar. 13, 2018

(54) ENHANCED ZEIN REDUCTION IN TRANSGENIC CORN SEED

(71) Applicant: Monsanto Technology LLC, St. Louis, MO (US)

(72) Inventors: Michael H. Luethy, Mystic, CT (US); Thomas M. Malvar, N. Stonington, CT (US); Shihshieh Huang, Woodland, CA (US)

(73) Assignee: Monsanto Technology LLC, St. Louis, MO (US)

( * ) Notice: Subject to any disclaimer, the term of this patent is extended or adjusted under 35 U.S.C. 154(b) by 528 days.

This patent is subject to a terminal disclaimer.

(21) Appl. No.: 13/914,505

(22) Filed: Jun. 10, 2013

(65) Prior Publication Data

US 2014/0173778 A1    Jun. 19, 2014

Related U.S. Application Data

(62) Division of application No. 12/277,196, filed on Nov. 24, 2008, now Pat. No. 8,461,418, which is a division of application No. 11/202,401, filed on Aug. 11, 2005, now abandoned.

(60) Provisional application No. 60/543,157, filed on Feb. 10, 2004, provisional application No. 60/543,187, filed on Feb. 10, 2004.

(51) Int. Cl.
| | | |
|---|---|---|
| A23K 1/14 | (2006.01) | |
| C07K 14/415 | (2006.01) | |
| C12N 9/06 | (2006.01) | |
| C12N 15/82 | (2006.01) | |
| A23K 10/30 | (2016.01) | |
| A23L 7/10 | (2016.01) | |

(52) U.S. Cl.
CPC ............. *A23K 1/14* (2013.01); *A23K 10/30* (2016.05); *A23L 7/198* (2016.08); *C07K 14/415* (2013.01); *C12N 9/0028* (2013.01); *C12N 15/8218* (2013.01); *C12N 15/8247* (2013.01); *C12N 15/8251* (2013.01); *C12N 15/8254* (2013.01)

(58) Field of Classification Search
CPC ...... A23K 1/14; C07K 14/415; C12N 9/0028; C12N 15/8218; C12N 15/8251; C12N 15/8254; C12N 15/8247; A23L 1/1041
USPC ....................................................... 800/286
See application file for complete search history.

(56) References Cited

U.S. PATENT DOCUMENTS

| | | | |
|---|---|---|---|
| 5,107,065 A | 4/1992 | Shewmaker et al. | |
| 5,231,020 A | 7/1993 | Jorgensen et al. | |
| 5,283,184 A | 2/1994 | Jorgensen et al. | |
| 5,508,468 A | 4/1996 | Lundquist et al. | |
| 5,759,829 A | 6/1998 | Shewmaker et al. | |
| 6,054,299 A | 4/2000 | Conrad | |
| 6,090,627 A | 7/2000 | Kemp et al. | |
| 6,160,208 A | 12/2000 | Lundquist et al. | |
| 6,326,193 B1 | 12/2001 | Liu et al. | |
| 6,326,527 B1 | 12/2001 | Kirihara et al. | |
| 6,329,574 B1 * | 12/2001 | Lundquist et al. | ........ 800/300.1 |
| 6,506,559 B1 | 1/2003 | Fire et al. | |
| 7,855,323 B2 * | 12/2010 | Huang et al. | .................. 800/286 |
| 9,006,414 B2 * | 4/2015 | Huang | ................... C07H 21/02 |
| | | | 435/320.1 |
| 2002/0048814 A1 | 4/2002 | Oeller | |
| 2003/0018993 A1 | 1/2003 | Gutterson et al. | |
| 2003/0036197 A1 | 2/2003 | Glassman et al. | |
| 2003/0175965 A1 | 9/2003 | Lowe et al. | |
| 2004/0029283 A1 | 2/2004 | Fillatti | |
| 2005/0176670 A1 | 8/2005 | Huang et al. | |
| 2005/0193444 A1 | 9/2005 | Malvar et al. | |
| 2005/0260754 A1 | 11/2005 | Kock et al. | |
| 2006/0064772 A1 | 3/2006 | Kriz et al. | |
| 2009/0158463 A1 | 6/2009 | Luethy et al. | |
| 2015/0191728 A1 * | 7/2015 | Huang | ................... C07H 21/02 |
| | | | 514/44 R |

FOREIGN PATENT DOCUMENTS

| | | |
|---|---|---|
| EP | 0 426 195 | 11/1990 |
| EP | 0 428 881 | 5/1991 |
| WO | WO 98/53083 | 5/1998 |
| WO | WO 98/26064 | 6/1998 |
| WO | WO 99/49029 | 3/1999 |
| WO | WO 99/53050 | 4/1999 |
| WO | WO 03/077643 | 9/2003 |
| WO | WO 03/078629 | 9/2003 |
| WO | WO 2005/077116 | 8/2005 |
| WO | WO 2007/024207 | 3/2007 |

OTHER PUBLICATIONS

Amendment and Response to Office Action regarding U.S. Appl. No. 11/057,062, dated Jan. 7, 2008.
Amendment and Response to Office Action regarding U.S. Appl. No. 11/057,062, dated Jul. 2, 2008.
Amendment and Response to Office Action regarding U.S. Appl. No. 11/202,401, dated Jun. 23, 2008.
Anonymous, "About CSIRO's hairpin RNAi," Retrieved from the Internet, http://www.p1.csiro.au/rnai/about.htm, undated, 2008.
Chuang et al., "Specific and heritable genetic interference by double-stranded RNA in *Arabidopsis thaliana*," *PNAS*, 97(9):4985-4990, 2000.
DeBuck et al., "Transgene silencing of invertedly repeated transgenes is released upon deletion of one of the transgenes involved," *Plant Mol. Biol.*, 46:433-445, 2001.

(Continued)

*Primary Examiner* — Li Zheng
(74) *Attorney, Agent, or Firm* — Dentons US LLP; Amanda Carmany-Rampey

(57) ABSTRACT

Anti-sense-oriented RNA gene suppression agents in the form of a loop of anti-sense-oriented RNA is produced in cells of transgenic organisms, e.g. plants, by transcription from a recombinant DNA construct that comprises in 5' to 3' order a promoter element operably linked to more than one anti-sense-oriented DNA element and one or more complementary DNA elements.

14 Claims, 8 Drawing Sheets

(56) References Cited

OTHER PUBLICATIONS

European Search Report for PCT/US2005/028615, Jun. 2, 2008.
Helliwell et al., "High-throughput vectors for efficient gene silencing in plants," *Funct. Plant Biol.*, 29:1217-1225, 2002.
Houmard et al., "High-lycine corn generated by endosperm-specific suppression of lysine catabolism using RNAi," *Plant Biotechnology J.*, 5:605-614, 2007.
Huang et al., "High lysine and high tryptophan transgenic maize resulting from the reduction of both 19- and 22-kD alpha-zeins," *Plant Molecular Biology*, 61(3):525-535, 2006.
Huang et al., "High-lysine corn produced by the combination of enhanced lysine biosynthesis and reduced zein accumulation," *Plant Biotechnology Journal*, 3:555-569, 2005.
Huang et al., "Improving nutritional quality of maize proteins by expressing sense and antisense zein genes," *J. Agric. Food Chem.*, 52:1958-1964, 2004.
Jorgensen et al., "T-DNA is organized predominantly in inverted repeat structures in plants transformed with *Agrobacterium tumefaciens* C58 derivatives," *Mol. Gen. Genet.*, 207:471-477, 1987.
Mette et al., "Production of aberrant promoter transcripts contributes to methylation and silencing of unlinked homologous promoters in trans," *The EMBO Journal*, 18:241-248, 1999.
Mette et al., "Transcriptional silencing and promoter methylation triggered by double-stranded RNA," *The EMBO Journal*, 19:5194-5201, 2000.
Office Action regarding U.S. Appl. No. 11/057,062, dated Apr. 2, 2008.
Office Action regarding U.S. Appl. No. 11/057,062, dated Sep. 5, 2007.
Office Action regarding U.S. Appl. No. 11/202,401, dated Feb. 21,2008.
Office Action regarding U.S. Appl. No. 11/202,401, dated Sep. 30, 2008.
PCT International Search Report for PCT/US05/28615, Oct. 30, 2006.
Rebowski et al., "Antisense hairpin loop oligonucleotides as inhibitors of expression of multidrug resistance-associated protein 1: their stability in fetal calf serum and human plasma," *ACTA Biochimica Polonica*, 48(4):1061-1076, 2001.
Redenbaugh et al., "Aminoglycoside 3'-phosphototransferase-II (APH) (3')II)—review of its safety and use in the production of genetically-engineered plants," Food Biotechnology, 8(2-3):137-165, 1994.
Redenbaugh et al., "Determination of the safety of genetically engineered crops," ACS Symposium Series 605:72-87, 1995.
Redenbaugh et al., "Regulatory assessment of the flavr-savr tomato," *Trends in Food Science & Technology*, 5(4):105-110, 1994.
Redenbaugh et al., "Regulatory issues for commercialization of tomatoes with an antisense polygalacturonase gene," *In Vitro Cellular & Developmental Biology—Plant*; 29P(1):17-26, 1993.
Redenbaugh et al., In: Safety assessment of genetically engineered fruits and vegetables, a case study of Flavr Savr Tomato, Redenbaugh of al. (Eds.) CRC Press, Boca Raton, FL, pp. 88-102, 1992.
Russell of al., "Tissue-specific expression in transgenic maize of four endosperm promoters from maize and riceZein Z27," *Transgenic Res.*, 6(2):157-168, 1997.
Sanders, "Tomato transgene structure and silencing," *Nature Biotechnology*, 23(3)"287-288, 2005.
Segal et al., "A new opaque variant of maize by a single dominant RNA-interference-inducing transgene," *Genetics*, 165:387-397, 2003.
Sijen et al., "RNA-mediated virus resistance: role of repeated transgenes and delineation of target regions," *The Plant Cell*, 8:2277-2294, 1996.
Smith et al., "Total silencing by intron-sliced hairpin RNAs," *Nature*, 407:319-320, 2000.
Stam et al., "Post-transcriptional silencing of chalcone synthase in petunia by inverted transgene repeats," *The Plant Journal*, 12:63-82, 1997.
Supplemental European Search Report dated Jul. 21, 2008.
Unger et al., "Dominant negative mutants of opaque2 suppress transactivation of a 22-kD zein promoter by opaque2 in maize endosperm cells," *The Plant Cell*, 5:831-841, 1993.
Waterhouse et al., "Virus resistance and gene silencing in plants can be induced by simultaneous expression of sense and antisense RNA," *Proc. Natl. Acad. Sci. USA*, 95:13959-13964, 1998.
Wesley et al., "Construct design for efficient, effective and high-throughput gene silencing in plants," *Plant Journal*, 27:581-590, 2001.

\* cited by examiner

No. of events analyzed: 29
No. of events displayed only 19-kD α-zeins reduction: 0
No. of events displayed both 19- and 22-kD α-zeins reduction: 26

No. of events analyzed: 14
No. of events displayed only 19-kD α-zeins reduction: 10
No. of events displayed both 19- and 22-kD α-zeins reduction: 2

In zein reduction lines the protein content of the kernels is correlated to their levels of free amino acids

ENHANCED ZEIN REDUCTION IN TRANSGENIC CORN SEED

CROSS REFERENCE TO RELATED APPLICATIONS

This application is a divisional of U.S. application Ser. No. 12/277,196, filed Nov. 24, 2008, now issued as U.S. Pat. No. 8,461,418, which application is a divisional of U.S. application Ser. No. 11/202,401, now abandoned, filed Aug. 11, 2005, which claims priority under 35 U.S.C. 119(e) to provisional applications Ser. No. 60/543,157, filed Feb. 10, 2004, No. 60/543,187 filed Feb. 10, 2004 and No. 60/600,859, filed Aug. 11, 2004; and to utility application Ser. No. 11/057,062, filed Feb. 10, 2005, the disclosures of all of which are incorporated herein by reference in their entireties.

INCORPORATION OF SEQUENCE LISTING

A computer readable form of the sequence listing is contained in the file named "53428B.ST25.txt" which is 21 kb (measured in MS-Windows) and was created on Feb. 9, 2005 and is located on a CDROM, which is filed herewith and herein incorporated by reference.

FIELD OF THE INVENTION

Disclosed herein are seeds for transgenic corn having elevated amino acid levels, recombinant DNA constructs for producing gene-suppressing loops of anti-sense RNA and methods of making and using such constructs and transgenic plants expressing gene-suppressing loops of anti-sense RNA.

BACKGROUND

Certain plants have low levels of specific amino acids compared to other plants, or compared to hypothetical nutritionally "perfect" protein models based on milk or egg. By these standards, corn has low levels of lysine, methionine and tryptophan. Efforts to increase amino acid levels in transgenic plants include expressing recombinant DNA which encodes proteins in an amino acid synthesis pathway at higher levels than native genes. One such gene for producing enhanced levels of lysine in corn is a bacterial dihydrodipicolinic acid synthase. A strategy for achieving even higher levels of amino acids includes suppression of genes encoding proteins in amino acid catabolic pathways.

Gene suppression includes any of the well-known methods for suppressing transcription of a gene or the accumulation of the mRNA corresponding to that gene, thereby preventing translation of the transcript into protein. More particularly, gene suppression by inserting a recombinant DNA construct with anti-sense oriented DNA to regulate gene expression in plant cells is disclosed in U.S. Pat. No. 5,107,065 (Shewmaker et al.) and U.S. Pat. No. 5,759,829 (Shewmaker et al.). Plants transformed using such anti-sense oriented DNA constructs for gene suppression can comprise integrated DNA arranged as an inverted repeat from co-insertion of several copies of the transfer DNA (T-DNA) into plants by *Agrobacterium*-mediated transformation, as disclosed by Redenbaugh et al. in "Safety Assessment of Genetically Engineered FLAVR SAVR Tomato, CRC Press, Inc. (1992). Inverted repeat insertions can make up a part or all of the T-DNA, e.g. the T-DNA can contain an inverted repeat of a complete or partial anti-sense construct. Screening for inserted DNA comprising inverted repeat elements can improve the efficiency of identifying transformation events effective for gene silencing when the transformation construct is a simple anti-sense DNA construct.

Gene suppression caused by an inserted recombinant DNA construct with sense-oriented DNA is disclosed in U.S. Pat. No. 5,283,184 (Jorgensen et al.) and U.S. Pat. No. 5,231,020 (Jorgensen et al.). Inserted T-DNA providing gene suppression in plants transformed with such sense constructs by *Agrobacterium* is organized predominantly in inverted repeat structures, as disclosed by Jorgensen et al., Mol. Gen. Genet., 207: 471-477 (1987). See also Stam et al., The Plant Journal, 12: 63-82 (1997) and De Buck et al., Plant Mol. Biol. 46 433-445 (2001), who used segregation studies to support Jorgensen's finding that in many events gene silencing is mediated by multimeric transgene T-DNA where the T-DNAs are arranged in inverted repeats. Screening for inserted DNA comprising inverted repeat elements can improve the gene silencing efficiency when transforming with simple sense-orientated DNA constructs.

Gene silencing can also be effected by transcribing RNA from both a sense and an anti-sense oriented DNA using two separate transcription units, e.g. as disclosed by Shewmaker et al. in U.S. Pat. No. 5,107,065 where in Example 1a binary vector was prepared with both sense and anti-sense aroA genes. Similar constructs are disclosed in International Publication No. WO 99/53050 (Waterhouse et al.). See also U.S. Pat. No. 6,326,193 where gene targeted DNA is operably linked to opposing promoters.

Gene suppression can be achieved in plants by using transformation constructs that are capable of generating an RNA that can form double-stranded RNA along at least part of its length. Gene suppression in plants is disclosed in EP 0426195 A1 (Goldbach et al.) where recombinant DNA constructs for transcription into hairpin RNA provided transgenic plants with resistance to tobacco spotted wilt virus. See also Sijen et al., The Plant Cell, Vol. 8, 2277-2294 (1996) which discloses the use of constructs carrying inverted repeats (sense followed by anti-sense) of a cowpea mosaic virus gene in transgenic plants to mediate virus resistance. See also International Publication No. 98/53083 (Grierson et al.) and related U.S. Patent Application Publication No. 2003/0175965 A1 (Lowe et al.) which disclose gene suppression using a double stranded RNA construct comprising a gene coding sequence preceded by an inverted repeat of the 5' UTR. Constructs for posttranscriptional gene suppression in plants by double-stranded RNA of the target gene are also disclosed in International Publication No. WO 99/53050 (Waterhouse et al.) and International Publication No. WO 99/49029 (Graham et al.). See also U.S. Patent Application Publication No. 2002/0048814 A1 (Oeller) where DNA constructs are transcribed to sense or anti-sense RNA with a hairpin-forming poly(T)-poly(A) tail. See also U.S. Patent Application Publication No. 2003/0018993 A1 (Gutterson et al.) where sense or anti-sense DNA is followed by an inverted repeat of the 3' untranslated region of the NOS gene. See also U.S. Patent Application Publication No. 2003/0036197 A1 (Glassman et al.) where RNA for reducing the expression of target mRNA comprises a segment with homology to target mRNA and a segment with complementary RNA regions that are unrelated to endogenous RNA.

The production of dsRNA in plants to inhibit gene expression, e.g. in a nematode feeding on the plant, is disclosed U.S. Pat. No. 6,506,559 (Fire et al.). Multi-gene suppression vectors for use in plants are disclosed in U.S. patent application Ser. No. 10/465,800 (Fillatti).

Transcriptional suppression such as promoter trans suppression can be effected by a expressing a DNA construct comprising a promoter operably linked to inverted repeats of promoter DNA from a target gene. Constructs useful for such gene suppression mediated by promoter trans suppression are disclosed by Mette et al., The EMBO Journal, Vol. 18, pp. 241-148, (1999) and by Mette et al., The EMBO Journal, Vol. 19, pp. 5194-5201-148, (2000), both of which are incorporated herein by reference.

All of the above-described patents, applications and international publications disclosing materials and methods for gene suppression in plants are incorporated herein by reference.

SUMMARY OF THE INVENTION

This invention provides methods and recombinant DNA constructs useful for producing anti-sense-oriented RNA for gene suppression in transgenic organisms. In one aspect of the invention a recombinant DNA construct for suppressing a plurality of target genes comprises in 5' to 3' order a promoter element operably linked to an anti-sense-oriented DNA element and a sense-oriented. DNA element, in which the sense-oriented DNA element is shorter than the anti-sense-oriented DNA element and sense-oriented RNA transcribed from the sense-oriented DNA is complementary to the 5'-most end of anti-sense-oriented RNA transcribed from the anti-sense-oriented DNA element, whereby the transcribed RNA forms a into a loop of anti-sense-oriented RNA for suppressing the plurality of target genes.

The sense-oriented DNA can be cloned as an inverted repeat of a 5'-most segment of the anti-sense-oriented DNA element. Constructs with such sense-oriented DNA are transcribed to RNA that forms a loop of anti-sense-oriented RNA closed at its ends with a double-stranded RNA (dsRNA) segment, e.g. as illustrated in FIG. 1. To form an anti-sense-oriented RNA loop the complementary DNA element is conveniently not more than about one-half the length of the anti-sense-oriented DNA element, and preferably not more than one-third the length of the anti-sense-oriented DNA element, e.g. not more than one-quarter the length of the anti-sense-oriented DNA element. The overall lengths of the combined DNA elements can vary. For instance, the anti-sense-oriented DNA element can consist of from 500 to 5000 nucleotides and the complementary DNA element can consist of from 50 to 500 nucleotides. In many cases it will be useful for the anti-sense-oriented DNA segment to be more than twice the length of the sense-oriented DNA segment to allow for formation of an anti-sense-oriented RNA loop.

The anti-sense transcription unit can be designed to suppress multiple genes where the DNA is arranged with two or more anti-sense-oriented elements from different genes targeted for suppression followed by a complementary sense-oriented element, e.g. complementary to at least a part of the 5' most anti-sense element.

This invention also provides methods of suppressing the expression of a gene by providing in the cells of a plant a recombinant DNA construct of this invention that transcribes to an anti-sense loop of RNA. In other aspects of the invention, e.g. for providing traits other than plants with enhanced amino acid, the gene targeted for suppression can be a plant gene, a plant pest gene, a plant pathogen gene or a combination thereof. In the constructs, methods and plants of this invention the gene targeted for silencing can be a native gene or an exogenous gene or a gene in an organism that ingests or contacts the tissues of the plant that have cells comprising anti-sense RNA in a loop according to this invention. Plant pathogens include viruses such as cucumber mosaic virus, bacteria such as *Erwinia stewartii* (Stewart's wilt of corn) and fungi such as *Phakopsora pachyrhizi* (soybean rust fungus); plant pests include nematodes such as soybean cyst nematode and root knot nematode, and insects of various orders including Lepidoptera (e.g., European corn borer), Coleoptera (e.g., spotted cucumber beetle) and Homoptera (e.g., aphids).

DETAILED DESCRIPTION

Figure 1:
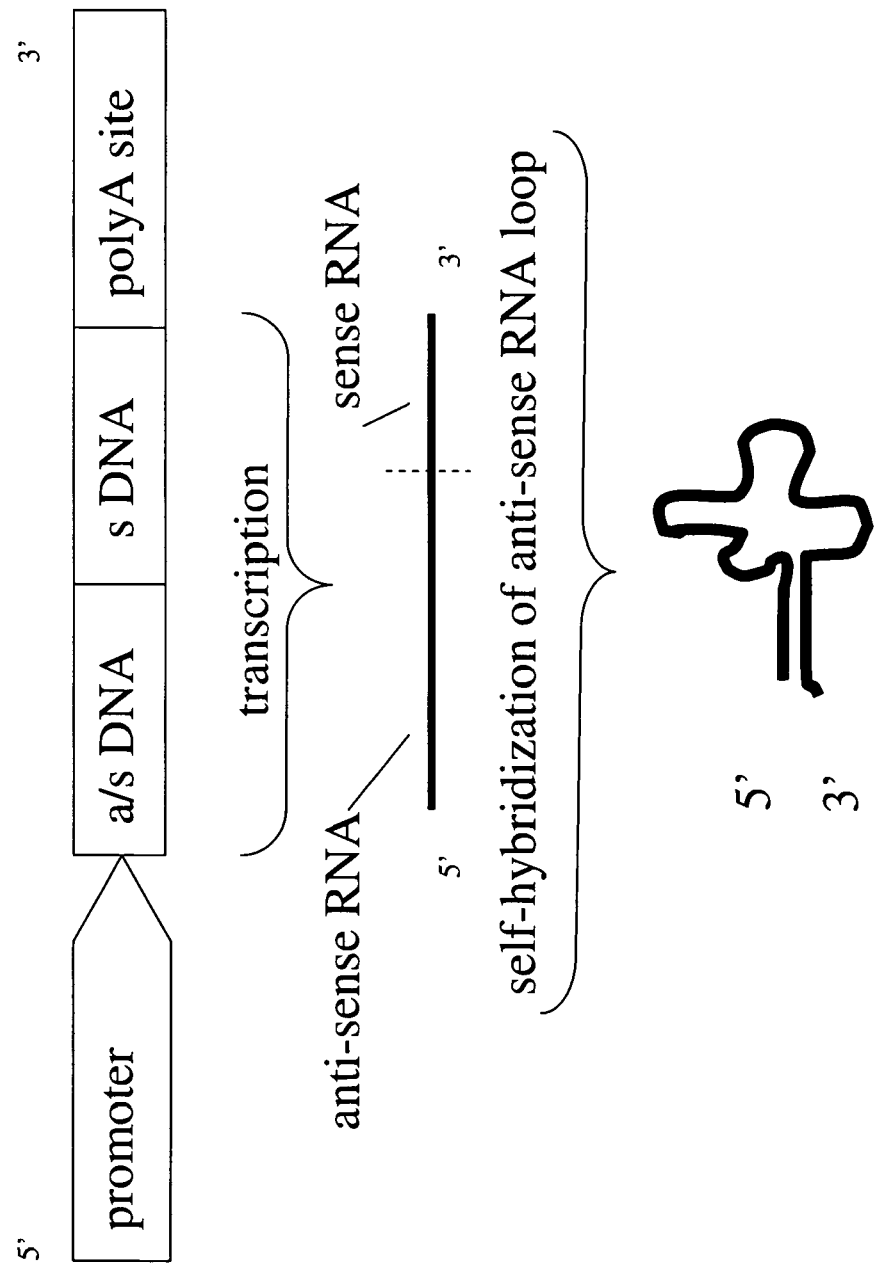
FIG. 1 is a schematic illustration of a recombinant DNA construct useful in this invention to produce an anti-sense-oriented loop of RNA.

SEQ ID NO:1 and SEQ ID NO:2 are nucleotide sequences of recombinant DNA constructs useful for transcribing RNA that can form an anti-sense-oriented RNA loop for suppressing one or multiple genes in transgenic plants. See Tables 1 and 2 for a description of elements of those constructs.

As used herein, "complementary" refers to polynucleotides that are capable of hybridizing, e.g. sense and anti-sense strands of DNA or self-complementary strands of RNA, due to complementarity of aligned nucleotides permitting C-G and A-T or A-U bonding.

As used herein "vector" means a DNA molecule capable of replication in a host cell and/or to which another DNA segment can be operatively linked so as to bring about replication of the attached segment. A plasmid is an exemplary vector.

As used herein a "transgenic" organism, e.g. plant or seed, is one whose genome has been altered by the incorporation of recombinant DNA comprising exogenous genetic material or additional copies of native genetic material, e.g. by transformation or recombination of the organism or an ancestral organism. Transgenic plants include progeny plants of an original plant derived from a transformation process including progeny of breeding transgenic plants with wild type plants or other transgenic plants. Crop plants of particular interest in the present invention include, but are not limited to maize, soybean, cotton, canola (rape), wheat, rice, sunflower, safflower and flax. Other crops of interest include plants producing vegetables, fruit, grass and wood.

Recombinant DNA Constructs for Plant Transformation

Recombinant DNA constructs for producing looped, anti-sense RNA, gene suppression agents in transgenic plants can be readily prepared by those skilled in the art. Typically, such a DNA construct comprises as a minimum a promoter active in the tissue targeted for suppression, a transcribable DNA element having a sequence that is complementary to nucleotide sequence of a gene targeted for suppression and a transcription terminator element. The targeted gene element copied for use in transcribable DNA in the gene suppression construct can be a promoter element, an intron element, an exon element, a 5' UTR element, or a 3'UTR element. Although the minimum size of DNA copied from sequence of a gene targeted for suppression is believed to be about 21 or 23 nucleotides; larger nucleotide segments are preferred, e.g. up the full length of a targeted gene. Useful lengths of either DNA segment are in the range of 50 to 5000 nucleotides, say anti-sense-oriented DNA of 500 to 5000 nucleotides in length and complementary DNA elements can be 50 to 500 or more nucleotides in length. The DNA element can comprise multiple parts of a gene, e.g. nucleotides that are complementary to contiguous or separated gene elements of UTR, exon and intron. Such constructs may also comprise other regulatory elements, DNA encoding transit peptides, signal peptides, selective markers and screenable markers as desired.

With reference to FIG. 1 there is schematically shown a recombinant DNA construct comprising a promoter element, an anti-sense-oriented DNA element (denoted "a/s DNA"), a complementary sense-oriented DNA element (denoted "s DNA") and DNA providing polyadenylation signals and site (denoted "polyA site"). The DNA construct is transcribed to RNA comprising an anti-sense-oriented RNA segment and a complementary RNA segment that is complementary to the 5'-most end of the anti-sense-oriented RNA segment. The 5' and 3' ends of the anti-sense RNA can self hybridize to form a double-stranded RNA segment that closes a loop of anti-sense-oriented RNA. For example, if the nucleotide sequence of the 5'-most end of the strand of transcribed anti-sense-oriented DNA is 5'-CGGCATA---, the sequence of the 3'-most end of the transcribed strand of the inverted repeat DNA will be ---TATGCCG-3' which is readily cloned from the source DNA providing the anti-sense element. With such sequences the loop of anti-sense-oriented RNA will extend from one side of a dsRNA segment, e.g.

```
5'-GCCGUAU--------
3'-CGGCAUA--------
```

The anti-sense-oriented DNA and its self-complementary DNA can be contiguous or separated by vector DNA, e.g. up to about 100 nucleotides or so of vector DNA separating restriction sites used for vector assembly.

Recombinant DNA constructs can be assembled using commercially available materials and methods known to those of ordinary skill in the art. A useful technology for building DNA constructs and vectors for transformation is the GATEWAY™ cloning technology (available from Invitrogen Life Technologies, Carlsbad, Calif.) uses the site specific recombinase LR cloning reaction of the Integrase att system from bacterophage lambda vector construction, instead of restriction endonucleases and ligases. The LR cloning reaction is disclosed in U.S. Pat. Nos. 5,888,732 and 6,277,608, U.S. Patent Application Publications 2001283529, 2001282319 and 20020007051, all of which are incorporated herein by reference. The GATEWAY™ Cloning Technology Instruction Manual that is also supplied by Invitrogen also provides concise directions for routine cloning of any desired DNA into a vector comprising operable plant expression elements.

An alternative vector fabrication method employs ligation-independent cloning as disclosed by Aslanidis, C. et al., Nucleic Acids Res., 18, 6069-6074, 1990 and Rashtchian, A. et al., Biochem., 206, 91-97, 1992 where a DNA fragment with single-stranded 5' and 3' ends are ligated into a desired vector that can then be amplified in vivo.

Numerous promoters that are active in plant cells have been described in the literature. These include promoters present in plant genomes as well as promoters from other sources, including nopaline synthase (nos) promoter and octopine synthase (ocs) promoters carried on tumor-inducing plasmids of *Agrobacterium tumefaciens*, caulimovirus promoters such as the cauliflower mosaic virus or figwort mosaic virus promoters. For instance, see U.S. Pat. Nos. 5,322,938 and 5,858,742 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 5,420,034 which discloses a napin promoter, U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429, 357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Pat. No. 6,635,806 which discloses a coixin promoter, U.S. 2002/0192813A1 which discloses 5', 3' and intron elements useful in the design of effective plant expression vectors, U.S. 2004/0216189 A1 which discloses a maize chloroplast aldolase promoter, and U.S. 2004/0123347A1 which discloses water-deficit inducible promoters, all of which are incorporated herein by reference. These and numerous other promoters that function in plant cells are known to those skilled in the art and available for use in recombinant polynucleotides of the present invention to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to effect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) Genetics 129:863-872), glutelin 1 (Russell (1997) supra), and peroxiredoxin antioxidant (Per1) (Stacy et al. (1996) *Plant Mol. Biol.* 31(6):1205-1216).

Recombinant DNA constructs prepared in accordance with the invention will often include a 3' element that typically contains a polyadenylation signal and site, especially if the recombinant DNA is intended for protein expression as well as gene suppression. Well-known 3' elements include those from *Agrobacterium tumefaciens* genes such as nos 3', tml 3', tmr 3', tms 3', ocs 3', tr7 3', e.g. disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

The gene-suppressing recombinant DNA constructs can also be stacked with DNA imparting other traits of agronomic interest including DNA providing herbicide resistance or insect resistance such as using a gene from *Bacillus thuringensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Persons of ordinary skill in the art are enabled in providing stacked traits by reference to U.S. patent application publications 2003/0106096A1 and 2002/0112260A1 and U.S. Pat. Nos. 5,034,322; 5,776,760; 6,107,549 and 6,376,754 and to insect/nematode/virus resistance by reference to U.S. Pat. Nos. 5,250,515; 5,880,275; 6,506,599; 5,986,175 and U.S. Patent Application Publication 2003/0150017 A1, all of which are incorporated herein by reference.

Transformation Methods—

Numerous methods for transforming plant cells with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, e.g. to replace an existing gene in the genome, to use an existing promoter in the plant genome, or to insert a recombinant polynucleotide at a predetermined site known to be active for gene expression. Several site specific recombination systems exist that are known to function implants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for screening of plants having an enhanced agronomic trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant that can be crossed with a second plant line to introgress the recombinant DNA into the second plant line. A transgenic plant with recombinant DNA providing an enhanced agronomic trait, e.g. enhanced yield, can be crossed with transgenic plant line having other recombinant DNA that confers another trait, e.g. herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line In the practice of transformation DNA is typically introduced into only a small percentage of target cells in any one transformation experiment. Marker genes are used to provide an efficient system for identification of those cells that are stably transformed by receiving and integrating a transgenic DNA construct into their genomes. Preferred marker genes provide selective markers that confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Screenable markers that provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Cells that survive exposure to the selective agent, or cells that have been scored positive in a screening assay, may be cultured in regeneration media and allowed to mature into plants. Developing plantlets can be transferred to plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, e.g. self-pollination is commonly used with transgenic corn. The regenerated transformed plant or its progeny seed or plants can be tested for expression of the recombinant DNA and screened for the presence of enhanced agronomic trait.

Transgenic Plants and Seeds

Transgenic plant seed provided by this invention are grown to generate transgenic plants having an enhanced trait as compared to a control plant. Such seed for plants with enhanced agronomic trait is identified by screening transformed plants or progeny seed for enhanced trait. For efficiency a screening program is designed to evaluate multiple transgenic plants (events) comprising the recombinant DNA, e.g. multiple plants from 2 to 20 or more transgenic events.

Transgenic plants grown from transgenic seed provided herein demonstrate improved agronomic traits that contribute to increased yield or other trait that provides increased plant value, including, for example, improved seed quality. Of particular interest are plants having enhanced yield resulting from improved plant growth and development, stress tolerance, improved seed development, higher light response, improved flower development, or improved carbon and/or nitrogen metabolism Many transgenic events that survive to fertile transgenic plants that produce seeds and progeny plants will not exhibit an enhanced agronomic trait. Screening is necessary to identify the transgenic plant having enhanced agronomic traits from populations of plants transformed as described herein by evaluating the trait in a variety of assays to detect an enhanced agronomic trait. These assays also may take many forms, including but not limited to, analyses to detect changes in the chemical composition, biomass, physiological properties, morphology of the plant.

The following examples illustrate aspects of the invention.

Example 1

This example illustrates preparation of a transformation vector useful for inserting a recombinant DNA construct of this invention into a transgenic plant to practice a method of this invention.

The LKR/SDH gene encodes a pre-protein for lysine ketoglutarate reductase (LKR) and saccharopine dehydrogenase (SDH) which are enzymes in a lysine catabolic pathway. Suppression of LKR is manifest in modification, e.g. increase, of lysine content. Suppression of LKR is effected by expressing in a plant a recombinant DNA construct that produces a stabilized anti-sense RNA transcribed from anti-sense-oriented LKR DNA and sense-oriented LKR DNA that forms a loop of anti-sense-oriented RNA.

A transformation vector is prepared comprising two transcription units between right and left borders from *Agrobacterium tumefaciens*. One transcription unit for a marker comprised:

(a) DNA of a rice actin promoter and rice actin intron,
(b) DNA of a chloroplast transit peptide from *Arabidopsis* EPSPS
(c) DNA of *A. tumefaciens* aroA (a glyphosate-resistant marker), and
(d) DNA of *A. tumefaciens* NOS terminator, The other transcription unit for LKR gene suppression comprised:

(a) DNA of *Zea mays* GLB1 promoter,
(b) DNA of a *Zea mays* ADH1 intron,
(c) Anti-sense-oriented DNA fragment of *Zea mays* LKR,
(d) Sense-oriented DNA fragment of *Zea mays* LKR, and
(e) DNA of *Zea mays* GLB1 terminator.

SEQ ID NO: 1 is DNA sequence of a transformation vector comprising the above-described marker and gene suppression elements. See Table 1 below for a description of the elements of the transformation vector contained within SEQ ID NO:1.

TABLE 1

| Bases of SEQ ID NO: 1 | Description of DNA segment |
|---|---|
| 1-357 | *A. tumefaciens* right border |
| 376-1774 | DNA of a rice actin promoter and rice actin intron |
| 1784-2011 | DNA of *A. tumefaciens* EPSPS chloroplast transit peptide |
| 2012-3379 | DNA of *A. tumefaciens* aroA (glyphosate-resistant marker) |
| 3395-3647 | DNA of *A. tumefaciens* NOS terminator |
| 3691-4686 | DNA of *Zea mays* Glb1 terminator |
| 4692-5145 | Sense-oriented DNA element from *Zea mays* LKR |
| 5152-6118 | Anti-sense-oriented DNA element from *Zea mays* LKR |
| 6123-6680 | DNA of a *Zea mays* ADH1 intron |
| 6687-8082 | DNA of *Zea mays* GLB1 promoter |
| 8149-8590 | *A. tumefaciens* left border |

Figure 2:
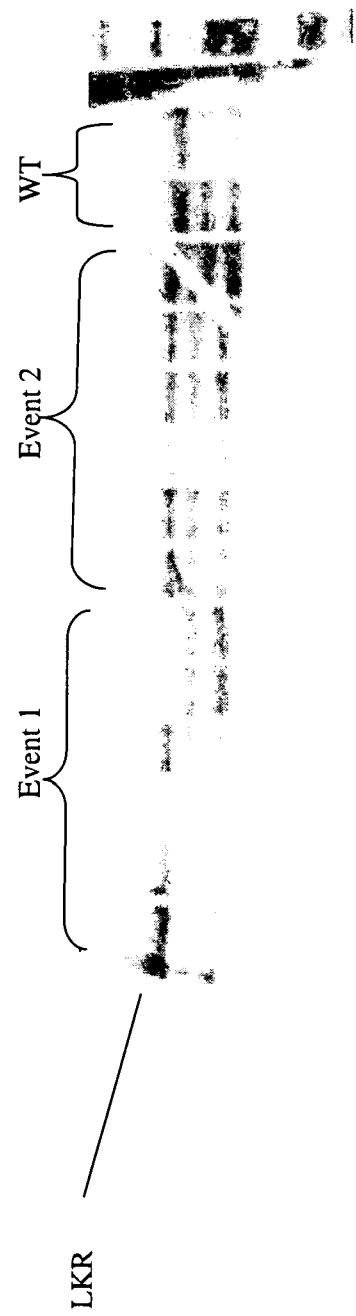
FIG. 2 is a Western analysis indicating gene suppression using a construct of this invention.

A vector prepared with the elements listed in Table 1 was used to transform corn plant tissue. Transgenic corn plants were obtained by *Agrobacterium*-mediated transformation. Transgenic plants from two separate transgenic insertion events were grown to produce F1 seed. Six mature seeds from each event were analyzed to determine success of transformation and suppression of LKR. The mature transgenic seeds were dissected to extract protein that was analyzed by Western analysis. With reference to FIG. 2, seed from one of the events showed no reduction in LKR as compared to wild type; and seed from the other event was shown to be segregating (1:1 hemizygous:wild type) as three of the six seeds showed substantial reduction in LKR as compared to wild type.

Example 2

This example illustrates a wide scope of embodiments of transformation vectors useful for inserting a recombinant DNA construct of this invention into a transgenic plant to practice a method of this invention. Transformation vectors were prepared using the following DNA elements where:

(a) "pGcx" refers to DNA for a promoter derived from a gamma coixin gene from *Coix lacryma-jobi*;

(b) "pZ27" refers to DNA for a promoter derived from a gamma zein gene from *Zea mays*;

(c) "pZ27t" refers to DNA for a truncated promoter having 59 nucleotides leader sequence deleted from the 3' region of pZ27;

(d) "Z19as" refers to DNA for an antisense-oriented segment of 351 nucleotides from the coding sequence of a 19 kilo dalton alpha zein gene from *Zea mays*;

(e) "Z19s" refers to DNA for a sense-oriented segment of 351 nucleotides from the coding sequence of a 19 kilo dalton alpha zein gene from *Zea mays*, which is an inverted repeat of Z19as;

(f) "Z22as" refers to DNA for an antisense-oriented segment of 789 nucleotides from the coding sequence of a 22 kilo dalton alpha zein gene from *Zea mays*;

(g) "Z22asL" refers to DNA for an antisense-oriented segment of 785 nucleotides from the coding sequence of a 22 kilo dalton alpha zein gene from *Zea mays*;

(h) "Z22asSI" refers to DNA for an antisense-oriented segment of 789 nucleotides from the coding sequence of a 22 kilo dalton alpha zein gene from *Zea mays* having a 520 nucleotide long spliceable intron from a GB 1 gene intron 3 from *Zea mays* inserted in the unpaired region;

(i) "Z22s" refers to DNA for a sense-oriented segment of 289 nucleotides from the coding sequence of a 22 kilo dalton alpha zein gene from *Zea mays*, which is an inverted repeat of the 5' end of Z22as; and (j) "TE9" refers to DNA for a sense oriented polyadenylation signal and site element from an RbcS2 gene from *Pisum sativum*.

With reference to Table 2 and SEQ ID NO:2 a transformation vector comprising "construct 2a" was made in the manner of Example 1 except that the transcription unit for LKR gene suppression was replaced by a transcription unit comprising the elements illustrated in the following schematic:

"Construct 2a" pZ27-Z19as-Z22asL-Z22s-Z19s-TE9

TABLE 2

| Bases of SEQ ID NO: 2 | description of DNA segment |
|---|---|
| 1-357 | *A. tumefaciens* right border |
| 376-1774 | DNA of a rice actin promoter and rice actin intron |
| 1784-2011 | DNA of *A. tumefaciens* EPSPS chloroplast transit peptide |
| 2012-3379 | DNA of *A. tumefaciens* aroA (glyphosate-resistant marker) |
| 3395-3647 | DNA of *A. tumefaciens* NOS terminator |
| 3479-4391 | DNA of *Pisum sativum* RbcS2 terminator |
| 4398-4748 | DNA for Z19s |
| 4755-5043 | DNA for Z22s |
| 5050-5835 | DNA of Z22asL |
| 5842-6192 | DNA of Z19as |
| 6204-7305 | DNA of *Zea mays* Z27 promoter |
| 7353-7794 | *A. tumefaciens* left border |

Corn callus was transformed and events with a single copy of the transformation vector were selected for growth into plants. Seed from plants grown from 26 of 29 single copy events showed substantial reduction of the 19 kilo dalton alpha zeins and the 22 kilo Dalton alpha zeins.

Other transformation vectors were made in a similar manner using the elements illustrated in the following Table 3.

TABLE 3

| Construct 2b1 | pGcx - Z19as - Z22asSI - Z22s - Z19s - TE9 |
| Construct 2b2* | pGcx - Z19as - Z22asSI - Z22s - Z19s - TE9 |
| Construct 2c | pZ27 - Z19as - Z22asSI - Z22s - Z19s - TE9 |
| Construct 2d | PZ27t - Z19as - Z22asSI - Z22s - Z19s - TE9 |
| Construct 2e | PZ27 - Z19as - Z22asL - Z19s - TE9 |

*construct 2b2 was inserted into a transformation vector that also included a transcription unit for expressing another gene having a promoter contiguous to pGcx.

Figure 3A:
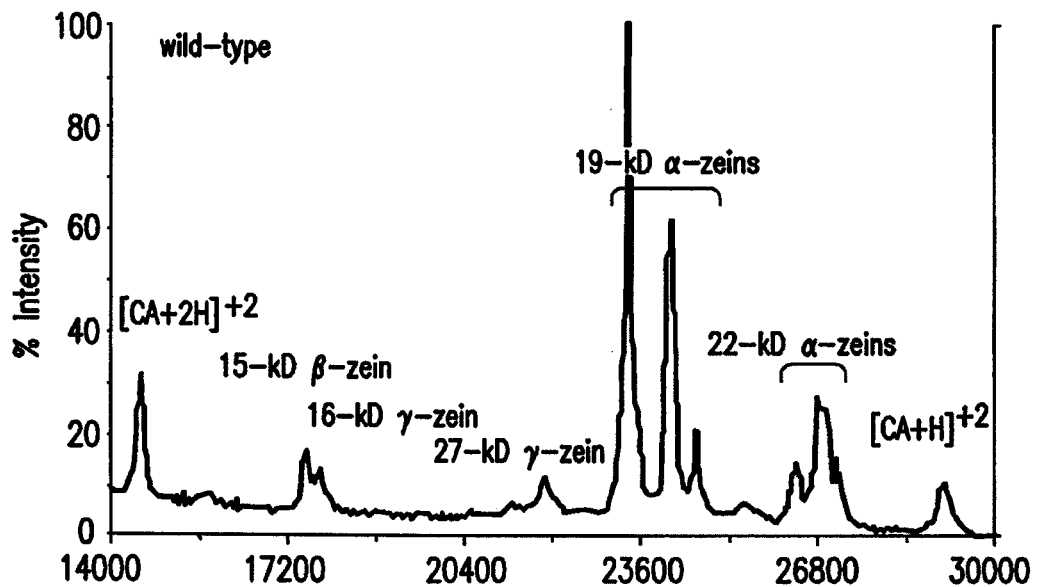
FIG. 3A through FIG. 3C show mass spectroscopy spectra indicating zein content seeds.
Figure 3B:
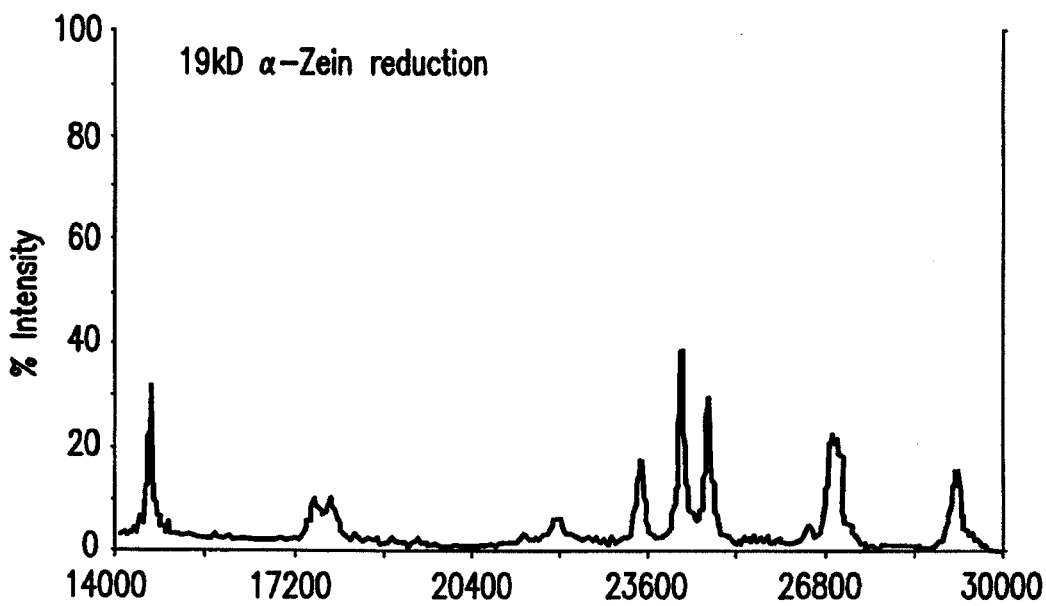
Figure 3C:
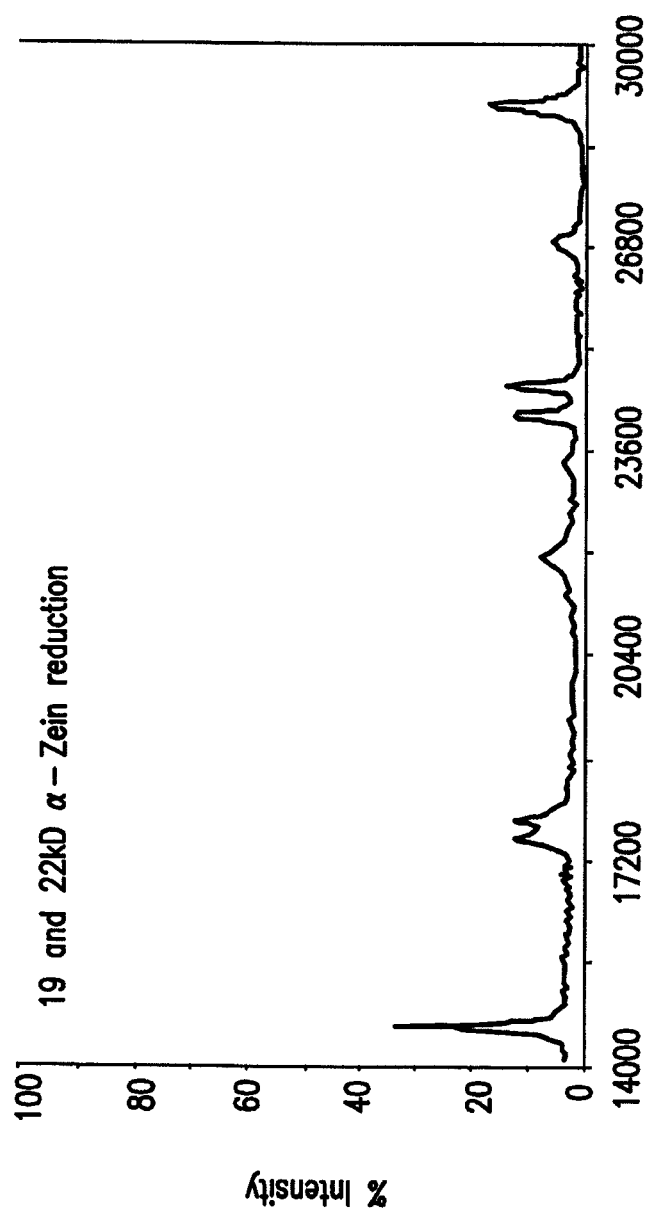

The efficiency of suppressing the alpha zeins in seeds produced by plants grown from single copy events is reported in Table 4 which reports the number of transgenic events with reduction of zeins as compared to the total number of transgenic events generated in each construct tested. The zein reduction phenotype is observed by MALDI-TOF MS (Matrix-Assisted-Laser-Desorption Ionization Time-Of-Flight Mass Spectrometry) analysis. FIG. 3 is illustrates typical spectra evidencing zein reduction.

TABLE 4

| Construct | 19 kD zein | 19 and 22 kD zein |
|---|---|---|
| 2a | 26/29 | 26/29 |
| 2b1 | 0/21 | 0/21 |
| 2b2 | 5/7 | 0/7 |
| 2c | 20/21 | 18/21 |
| 2d | 7/8 | 1/8 |
| 2e | 12/14 | 2/14 |

Example 3

This example illustrates zein reduction in transgenic plants harboring construct 2a (pMON73567; Table 2 and FIG. 4A) and construct 2e (pMON73566; Table 3, Table 5, and FIG. 4B) as well as the oil, protein, and amino acid profiles of bulked kernels derived from plants grown from single copy events as reported in Table 4.

With reference to Table 5 and SEQ ID NO:2 a transformation vector comprising "construct 2e" was made in the manner of Example 1 except that the transcription unit for LKR gene suppression was replaced by a transcription unit comprising the elements illustrated in the following schematic:

"Construct 2e" PZ27-Z19as-Z22asL-Z19s-TE9

TABLE 5

| Bases of SEQ ID NO: 2 | description of DNA segment |
|---|---|
| 1-357 | *A. tumefaciens* right border |
| 376-1774 | DNA of a rice actin promoter and rice actin intron |
| 1784-2011 | DNA of *A. tumefaciens* EPSPS chloroplast transit peptide |
| 2012-3379 | DNA of *A. tumefaciens* aroA (glyphosate-resistant marker) |
| 3395-3647 | DNA of *A. tumefaciens* NOS terminator |
| 3479-4391 | DNA of *Pisum sativum* RbcS2 terminator |
| 4398-4748 | DNA for Z19s |
| 4750-5535 | DNA of Z22asL |
| 5542-5892 | DNA of Z19as |
| 5904-7003 | DNA of *Zea mays* Z27 promoter |
| 7353-7794 | *A. tumefaciens* left border |

Corn immature embryo was transformed and events with a single copy of the transformation vector were selected for growth into plants. Seed from plants grown from 2 of 14 single copy events showed substantial reduction of both the 19 kilo Dalton alpha zeins and the 22 kilo Dalton alpha zeins (Table 4).

Zein Reduction

Figure 4A:
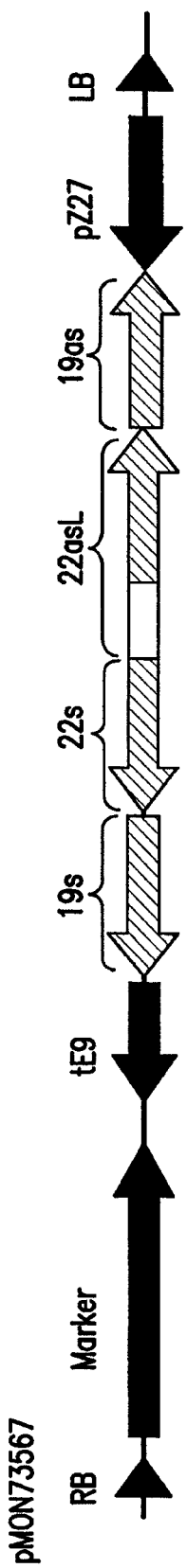
FIG. 4A and FIG. 4B are graphic illustrations of the design of the vector constructs used in an aspect of this invention.
Figure 4B:
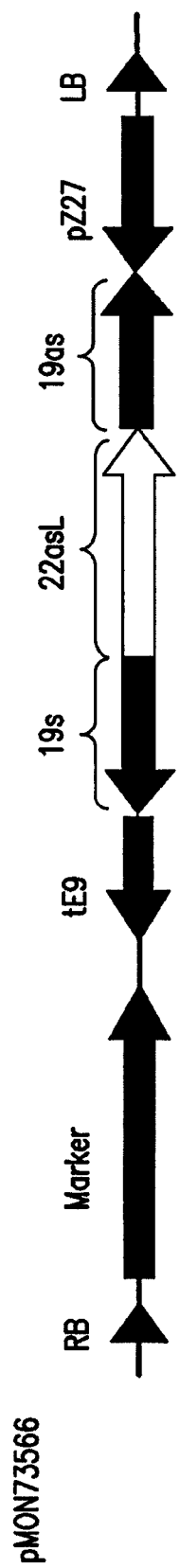
Figure 5A:
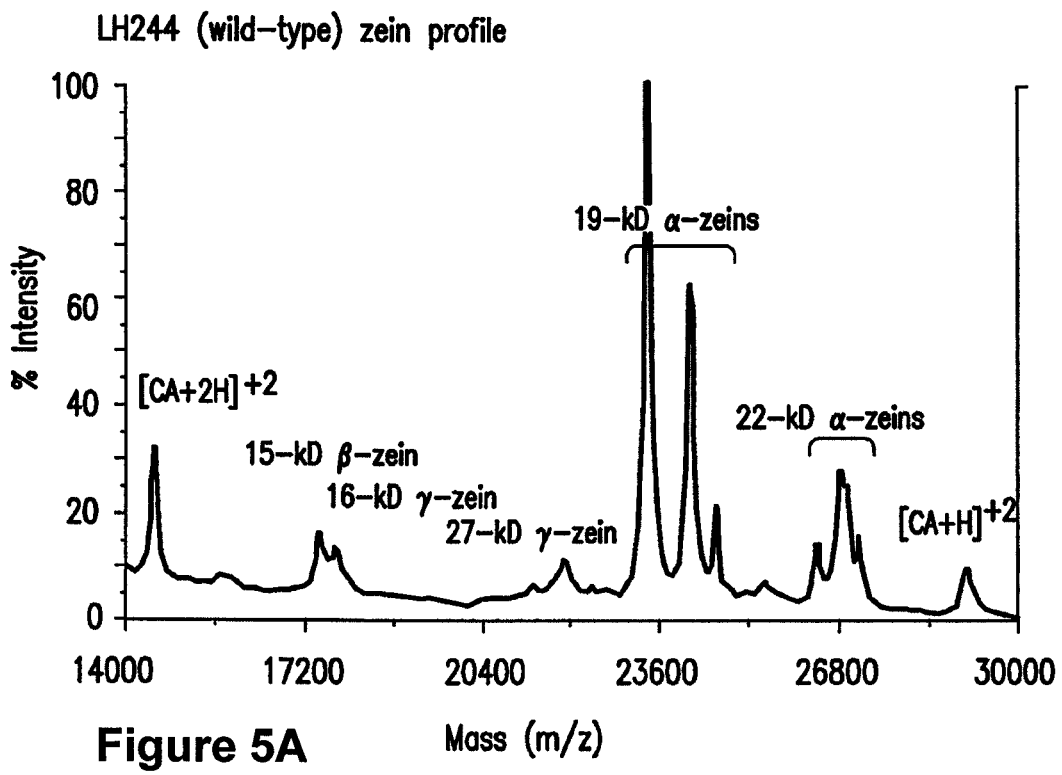
FIG. 5A through FIG. 5C show mass spectroscopy spectra indicating zein in wild type and transgenic seeds.
Figure 5B:
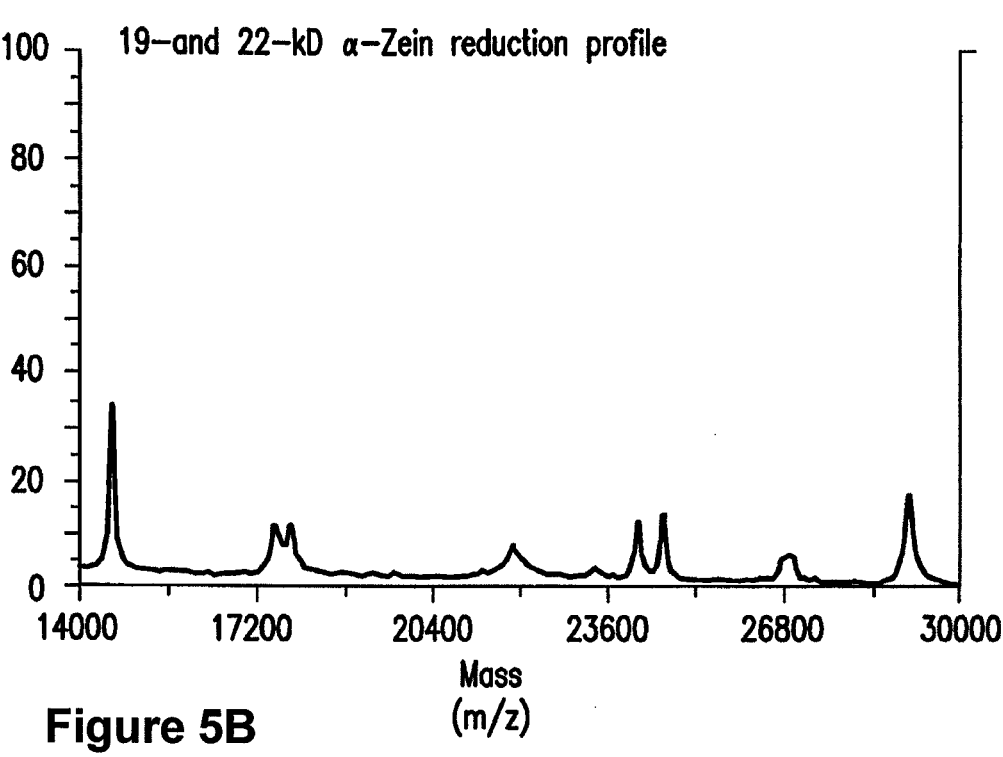
Figure 5C:
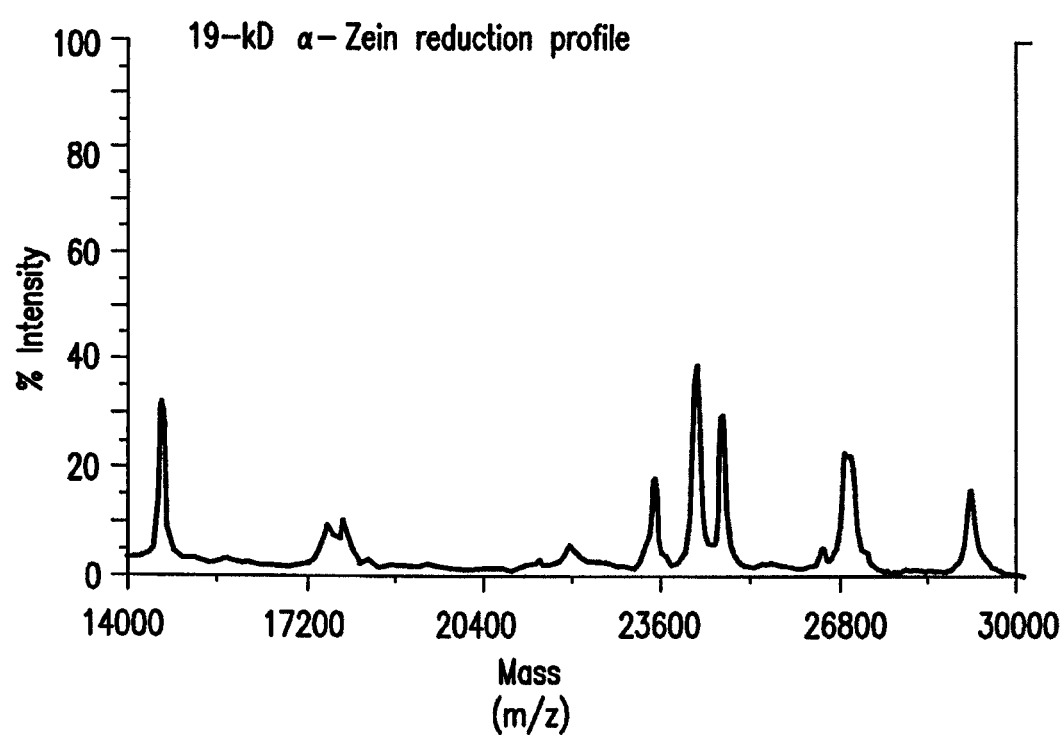

In transgenic plants harboring pMON73567, which contains dsRNA against both 19- and 22-kD α-zein sequences, 26 of 29 plants display reduction in both 19- and 22-kD α-zein accumulation (Table 4, construct 2a; FIG. 4A; FIG. 5B). Additionally, in transgenic plants harboring pMON73566, which contains dsRNA against only a 19-kD α-zein sequence and which uses the 22-kD α-zein sequence as the loop, 2 of 14 plants display reduction in both 19- and 22-kD α-zein accumulation (Table 4, construct 2e; FIG. 4B; FIG. 5B). Ten other pMON73566 events exhibit mostly 19-kD α-zein reduction (Table 4, construct 2e; FIG. 4B; FIG. 5C). Two representative events were selected from each construct for advancement to the next generation for collection of homozygous ears for compositional analyses. Events M80442 and M82186 containing the pMON73567 construct, and events M80780 and M80791 containing the pMON73566 construct were selected. M80442, M82186 and M80791 exhibit both 19- and 22-kD α-zein reduction. M80780, exhibits only 19-kD α-zein reduction.

Oil Content

Four events (M80442, M82186, M80780 and M80791) from 2 zein reduction constructs, pMON73566 and pMON73567, were grown in the field and zygosity was determined by a molecular assay. Oil was determined for kernels of homozygous transgene-positive ears and control ears by a wet chemistry oil extraction method. About 100 mg of ground sample was weighed in an 11-ml pressure cell half filled with sand. Additional sand was added to fill the cell, a filter was placed on the top, and the cell was capped with a screw cap. The cell was placed on the carousel of the Dionex Accelerated Solvent Extractor (Dionex, Sunnyvale, Calif.) following the manufacturer's protocol. The oil was extracted with petroleum ether at 1000 psig (pounds per square inch gauge) at 105° C. in three extraction steps. The final extraction product was added to a pre-weighed vial. The solvent was evaporated at 37° C. for two hours under a stream of either nitrogen or air and the vial was then weighed. Analysis of oil content of the samples was done in triplicate. Oil concentration of control kernels averaged 3.8% (Table 6). Average oil concentration of the transgene-positive kernels ranged from 4.0% to 5.2%. The average oil content of seeds from all 4 transgenic events represents an increase over the average oil content of seeds from wild type plants; and the increase in oil content from the M82186 event is considered to be statistically significant.

TABLE 6

Proximate assay and size of bulked kernels

| | | % ±SD$^a$ | | | |
|---|---|---|---|---|---|
| | Wild Type | pMON73566 | | pMON73567 | |
| | LH244 | M80780 | M80791 | M80442 | M82186 |
| Oil$^b$ | 3.8 ± 0.3 | 4.1 ± 0.2 | 4.4 ± 0.1 | 4.0 ± 0.5 | 5.2 ± 0.5 |
| Protein | 9.6 ± 1.1 | 8.7 ± 1.0 | 9.9 ± 1.2 | 9.3 ± 1.0 | 10.0 ± 0.7 |
| Starch | 70.4 ± 0.9 | 68.7 ± 0.4 | 67.3 ± 0.3 | 68.5 ± 0.6 | 67.8 ± 1.0 |
| Moisture | 9.0 ± 0.4 | 10.5 ± 0.2 | 10.4 ± 0.3 | 10.5 ± 0.2 | 10.5 ± 0.7 |
| Density | 1.31 ± 0.00 | 1.20 ± 0.01 | 1.20 ± 0.02 | 1.20 ± 0.01 | 1.21 ± 0.01 |
| Size$^c$ | 24.9 ± 1.4 | 24.3 ± 2.0 | 24.0 ± 0.9 | 23.9 ± 1.4 | 23.2 ± 2.2 |

Table 6. The oil, protein and starch contents are calculated on dry matter base. Except oil, the proximate contents of bulked kernels from each ear were determined by near infrared transmission (NIT) analysis.
$^b$The oil content was obtained by a wet chemistry method. The numbers in bold are statistically different from the LH244 numbers by Dunnett's test ($\alpha = 0.05$).
$^a$Data are means ± standard deviations.
$^c$The sizes were measured in 100 kernel weights in grams.

Amino Acid Profile

Transgenic plants transformed with antisense constructs targeting 19-kD α-zeins have exhibited an increased lysine content of up to 35% in mature corn seeds (Huang et al., 2004; Huang et al., 2005). In the transgenic plants haboring the pMON73567 and pMON73566 constructs that target both the 19- and 22-kD α-zeins, the increases in lysine content are significantly greater. As shown in Table 7, among the events analyzed, the least increase in lysine content, 66% ((4035 ppm transgenic-2438 ppm wild type)/2438 ppm wild type), is observed in M80780 and the most, 105% ((5003 ppm transgenic-2438 ppm wild type)/2438 ppm wild type), is found in M80791. Similarly, the transgenic plants have much higher tryptophan contents as compared to the wild type, LH244 (Table 7).

TABLE 7

Total amino acid analysis of ground kernels

| | | Ave ± SD$^a$ | | | |
|---|---|---|---|---|---|
| | Wild Type | PMON73566 | | PMON73567 | |
| | LH244 | M80780 | M80791 | M80442 | M82186 |
| Ala | 6687 ± 594 | 5497 ± 631 | 6417 ± 855 | 5862 ± 999 | 6458 ± 322 |
| Arg | 4342 ± 293 | 6060 ± 708 | 7313 ± 1048 | 6665 ± 1203 | 7165 ± 655 |
| Asx | 5555 ± 377 | 8928 ± 1651 | 11977 ± 2034 | 10253 ± 2803 | 11143 ± 886 |
| Glx | 17788 ± 1623 | 15873 ± 2421 | 18610 ± 2762 | 16860 ± 3617 | 18603 ± 1322 |

TABLE 7-continued

Total amino acid analysis of ground kernels

| | Ave ± SD[a] | | | | |
|---|---|---|---|---|---|
| | Wild Type | PMON73566 | | PMON73567 | |
| | LH244 | M80780 | M80791 | M80442 | M82186 |
| Gly | 3400 ± 166 | 4537 ± 463 | 5377 ± 770 | 4973 ± 783 | 5290 ± 410 |
| His | 1498 ± 126 | 2350 ± 234 | 2253 ± 441 | 2305 ± 518 | 2470 ± 160 |
| Ile | 3265 ± 255 | 3030 ± 368 | 3700 ± 678 | 3373 ± 587 | 3578 ± 261 |
| Leu | 11265 ± 1074 | 7318 ± 788 | 8327 ± 1106 | 7718 ± 1264 | 8270 ± 497 |
| Lys | 2438 ± 132 | 4035 ± 574 | 5003 ± 866 | 4533 ± 780 | 4800 ± 443 |
| Phe | 3760 ± 282 | 3032 ± 295 | 3637 ± 506 | 3288 ± 571 | 3455 ± 260 |
| Ser | 4067 ± 364 | 4235 ± 465 | 4620 ± 425 | 4355 ± 779 | 4785 ± 325 |
| Thr | 3062 ± 226 | 3572 ± 406 | 4047 ± 446 | 3783 ± 676 | 4130 ± 279 |
| Trp | 598 ± 48 | 877 ± 117 | 1087 ± 158 | 940 ± 201 | 1040 ± 96 |
| Tyr | 3720 ± 307 | 3430 ± 414 | 4093 ± 432 | 3652 ± 624 | 4045 ± 270 |
| Val | 4710 ± 325 | 5312 ± 598 | 6553 ± 1068 | 5977 ± 1030 | 6293 ± 483 |
| Sum | 76155 ± 5996 | 78087 ± 10057 | 93013 ± 12760 | 84535 ± 16220 | 91553 ± 6286 |
| Lys % (P)[b] | 2.83 ± 0.23 | 5.23 ± 0.17 | 5.62 ± 0.29 | 5.40 ± 0.37 | 5.33 ± 0.28 |
| Trp % (P)[b] | 0.69 ± 0.05 | 1.14 ± 0.04 | 1.22 ± 0.03 | 1.12 ± 0.11 | 1.15 ± 0.05 |
| Leu % (P)[b] | 13.00 ± 0.34 | 9.51 ± 0.15 | 9.38 ± 0.12 | 9.21 ± 0.56 | 9.20 ± 0.34 |

Table 7. Samples were ground mills of bulked mature kernels of individual ears.
[a]Data (ppm) are averages of ears within an event ± standard deviations. Four homologous ears from each event were measured.
[b]They are expressed as the percentages of protein measured in Table 6 without the subtraction of moisture. The numbers in bold are statistically different from the LH244 numbers by Dunnett's test ($\alpha = 0.05$). Asx, asparagine and Aspartate; Glx, glutamine and glutamate.

Figure 6:
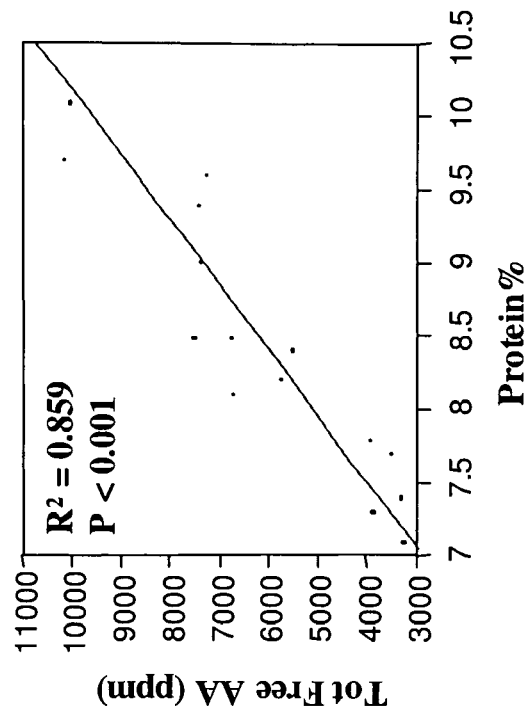
FIG. 6 illustrates the correlation between the protein content of the kernels and their levels of free amino acids.

Aspartate, asparagine and glutamate are among the free amino acids that exhibit a significant increase in the seeds of these transgenic plants (Table 8). The increased accumulation of these free amino acids has been shown to enhance lysine biosynthesis in the presence of CordapA (Huang et al., 2005; Monsanto patent application Ser. No. 11/077,089, filed Mar. 10, 2005).

the amount of protein accumulation is proportional to the level of free amino acids (FIG. 6). These results suggest a possible synergistic effect of combining zein reduction and the expression of asparagine synthetase that could result in improving both the quantity and the quality of the maize proteins.

TABLE 8

Free amino acid analysis of ground kernels

| | Ave ± SD[a] | | | | |
|---|---|---|---|---|---|
| | Wid Type | pMON73566 | | pMON73567 | |
| | LH244 | M80780 | M80791 | M80442 | M82186 |
| Ala | 95 ± 39 | 114 ± 73 | 194 ± 91 | 172 ± 103 | 313 ± 122 |
| Arg | 50 ± 24 | 92 ± 64 | 121 ± 40 | 110 ± 53 | 160 ± 38 |
| Asn | 232 ± 40 | 2341 ± 667 | 3726 ± 1102 | 2844 ± 1184 | 2995 ± 402 |
| Asp | 143 ± 30 | 692 ± 386 | 1306 ± 375 | 1040 ± 479 | 1323 ± 207 |
| Glu | 256 ± 33 | 582 ± 492 | 1064 ± 472 | 823 ± 670 | 1207 ± 119 |
| Gln | 85 ± 56 | 182 ± 186 | 270 ± 180 | 255 ± 264 | 319 ± 40 |
| Gly | 18 ± 6 | 25 ± 13 | 37 ± 13 | 31 ± 15 | 44 ± 7 |
| His | 24 ± 4 | 47 ± 21 | 79 ± 25 | 63 ± 27 | 76 ± 5 |
| Ile | 13 ± 5 | 18 ± 12 | 25 ± 8 | 21 ± 9 | 36 ± 9 |
| Leu | 10 ± 3 | 15 ± 14 | 25 ± 11 | 19 ± 14 | 34 ± 10 |
| Lys | 25 ± 12 | 40 ± 26 | 66 ± 39 | 57 ± 40 | 70 ± 11 |
| Phe | 37 ± 30 | 19 ± 12 | 34 ± 8 | 25 ± 11 | 40 ± 11 |
| Ser | 50 ± 21 | 69 ± 41 | 115 ± 50 | 88 ± 53 | 176 ± 76 |
| Thr | 16 ± 6 | 46 ± 41 | 84 ± 36 | 60 ± 46 | 110 ± 29 |
| Trp | 8 ± 1 | 17 ± 5 | 23 ± 4 | 21 ± 5 | 25 ± 1 |
| Tyr | 34 ± 6 | 94 ± 52 | 163 ± 18 | 120 ± 48 | 182 ± 52 |
| Val | 33 ± 10 | 46 ± 32 | 76 ± 29 | 62 ± 33 | 101 ± 26 |
| Sum | 1134 ± 259 | 4447 ± 1962 | 7417 ± 2334 | 5819 ± 3052 | 7225 ± 336 |

Table 8. Samples were ground mills of bulked mature kernels of individual ears.
[a]Data (ppm) are averages of ears within an event ± standard deviations. Four homologous ears from each event were measured. The numbers in bold are statistically different from the LH244 numbers by Dunnett's test ($\alpha = 0.05$).

Protein Content

The constitutive expression of asparagine synthetase is thought to increase the protein content of maize seeds by fueling the flux of free amino acids from vegetative tissues into developing ears. Not only do these zein reduction lines have elevated levels of free amino acids (Table 8), but also This invention contemplates the use of anti-sense-oriented DNA elements and sense-oriented DNA elements from other maize zein proteins, including but not limited to additional members of the 19- and 22-kD α-zeins, 16- and 27-kD γ-zeins, 10-kD δ-zeins, and 15-kD β-zeins, as a method for suppressing transcription of more than one gene or the accumulation of the mRNA corresponding to those genes thereby preventing translation of the transcript into protein. In particular, the contemplated α-zeins include all variants in the 19-kD size range and all variants in the 22-kD size range.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for generating maize seeds having at least one of enhanced lysine, enhanced oil and enhanced tryptophan comprising the steps of: a) transforming a maize plant cell with the recombinant DNA construct for suppression of a plurality of maize zein target genes, comprising in 5' to 3' order a promoter element operably linked to a plurality of anti-sense-oriented DNA elements from a plurality of maize zein target genes, the anti-sense-oriented DNA elements designated in 5' to 3' order element 1, element 2, and a plurality of sense-oriented DNA elements from a plurality of maize zein target genes, designed in 5' to 3' order element 3, element 4, wherein the anti-sense-oriented DNA element 2 has at least a portion of its sequence at its 3' end that is not complementary either to itself or to the sense-oriented DNA element 3, and wherein sense-oriented RNA transcribed by the sense-oriented DNA elements is complementary to the 5'-most end of anti-sense-oriented RNA transcribed by the anti-sense-oriented DNA elements; and b) regenerating the maize plant cell into a fertile transgenic maize plant, wherein the maize plant contains the construct in its genome; and c) harvesting seed from the maize plant, wherein the seed has at least one of enhanced lysine, enhanced oil and enhanced tryptophan relative to seed of the same variety not transformed with the construct.

2. A method for generating maize seeds having at least one of enhanced lysine, enhanced oil and enhanced tryptophan comprising the steps of: transforming a maize plant cell with the recombinant DNA construct for suppression of more than one maize zein target gene that comprises in 5' to 3' order a promoter element operably linked to more than one anti-sense-oriented DNA element from more than one maize zein target gene, the anti-sense-oriented DNA elements designed in 5' to 3' order element 1, element 2, and at least one sense-oriented DNA element from at least one maize zein target gene, designated element 3, wherein the anti-sense-oriented DNA element 2 has at least a portion of its sequence at its 3' end that is not complementary either to itself or to the sense-oriented DNA element 3, and sense-oriented RNA transcribed by the sense-oriented DNA element is complementary to the 5'-most end of anti-sense-oriented RNA transcribed by the anti-sense-oriented DNA element(s); and regenerating the maize plant cell into a fertile transgenic maize plant, wherein the maize plant contains the construct in its genome; and harvesting seed from the maize plant, wherein the seed has at least one of enhanced lysine, enhanced oil and enhanced tryptophan relative to seed of the same variety not transformed with the construct.

3. A transgenic maize plant comprising within its genome a DNA construct of for suppression of a plurality of maize zein target genes, comprising in 5' to 3' order a promoter element operably linked to a plurality of anti-sense-oriented DNA elements from a plurality of maize zein target genes, the anti-sense-oriented DNA elements designated in 5' to 3' order element 1, element 2, and a plurality of sense-oriented DNA elements from a plurality of maize zein target genes, designed in 5' to 3' order element 3, element 4, wherein the anti-sense-oriented DNA element 2 has at least a portion of its sequence at its 3' end that is not complementary either to itself or to the sense-oriented DNA element 3, and wherein sense-oriented RNA transcribed by the sense-oriented DNA elements is complementary to the 5'-most end of anti-sense-oriented RNA transcribed by the anti-sense-oriented DNA elements.

4. A harvested seed from the maize plant of claim 3, wherein the seed comprises the DNA construct.

5. A harvested seed from the maize plant of claim 3, wherein the seed comprises the DNA construct, and wherein the sense-oriented DNA elements are from two genes targeted for suppression and the anti-sense-oriented DNA elements are from two genes targeted for suppression.

6. A processed product of the seed of claim 4, wherein the product is a feed, a meal, or a partially purified protein composition that comprises the DNA construct.

7. A transgenic maize plant comprising within its genome a DNA construct for suppression of more than one maize zein target gene that comprises in 5' to 3' order a promoter element operably linked to more than one anti-sense-oriented DNA element from more than one maize zein target gene, the anti-sense-oriented DNA elements designed in 5' to 3' order element 1, element 2, and at least one sense-oriented DNA element from at least one maize zein target gene, designated element 3, wherein the anti-sense-oriented DNA element 2 has at least a portion of its sequence at its 3' end that is not complementary either to itself or to the sense-oriented DNA element 3, and sense-oriented RNA transcribed by the sense-oriented DNA element is complementary to the 5'-most end of anti-sense-oriented RNA transcribed by the anti-sense-oriented DNA element(s).

8. A harvested seed from the maize plant of claim 7, wherein the seed comprises the DNA construct.

9. A harvested seed from the maize plant of claim 7, wherein the seed comprises the DNA construct, and wherein the sense-oriented DNA element is from one gene targeted for suppression and the anti-sense-oriented DNA elements are from two genes targeted for suppression.

10. A processed product of the seed of claim 8, wherein the product is a feed, a meal, or a partially purified protein composition that comprises the DNA construct.

11. The method of claim 1, wherein said plurality of maize zein target genes is selected from the group consisting of 19- and 22-kD α-zeins, 16- and 27-kD γ-zeins, 10-kD δ-zeins, and 15-kD β-zeins.

12. The method of claim 2, wherein said more than one maize zein target gene is selected from the group consisting of 19- and 22-kD α-zeins, 16- and 27-kD γ-zeins, 10-kD δ-zeins, and 15-kD β-zeins and wherein the at least one maize zein target gene is selected from the group consisting of 19- and 22-kD α-zeins, 16- and 27-kD γ-zeins, 10-kD δ-zeins, and 15-kD β-zeins.

13. The transgenic maize plant of claim 3, wherein said plurality of maize zein target genes is selected from the group consisting of 19- and 22-kD α-zeins, 16- and 27-kD γ-zeins, 10-kD δ-zeins, and 15-kD β-zeins.

14. The transgenic maize plant of claim 7, wherein said more than one maize zein target gene is selected from the group consisting of 19- and 22-kD α-zeins, 16- and 27-kD γ-zeins, 10-kD δ-zeins, and wherein the at least one maize zein target gene is selected from the group consisting of 19- and 22-kD α-zeins, 16- and 27-kD γ-zeins, 10-kD δ-zeins, and 15-kD β-zeins.

* * * * *

UNITED STATES PATENT AND TRADEMARK OFFICE
CERTIFICATE OF CORRECTION

PATENT NO. : 9,913,487 B2  
APPLICATION NO. : 13/914505  
DATED : March 13, 2018  
INVENTOR(S) : Michael H. Luethy et al.

Page 1 of 1

It is certified that error appears in the above-identified patent and that said Letters Patent is hereby corrected as shown below:

On the Title Page

Item (62), please insert --This application 13/914,505 is a continuation-in-part of 12/973,821 filed Dec. 20, 2010, now Pat No. 9,006,414 which is a continuation of 11/057,062 filed Feb. 10, 2005, now Pat. No. 7,855,323--

Item (60), please insert --Provisional application No. 60/600,859 filed Aug. 11, 2004--

Signed and Sealed this  
Twenty-sixth Day of March, 2019

Andrei Iancu  
*Director of the United States Patent and Trademark Office*

```
                        SEQUENCE LISTING

<160> NUMBER OF SEQ ID NOS: 2

<210> SEQ ID NO 1
<211> LENGTH: 8590
<212> TYPE: DNA
<213> ORGANISM: Artificial
<220> FEATURE:
<223> OTHER INFORMATION: Recombinant construct

<400> SEQUENCE: 1 aggattttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgccct tttaaatatc cgattattct aataaacgct cttttctctt aggtttaccc     300
gccaatatat cctgtcaaac actgatagtt taaactgaag gcgggaaacg acaatctgat     360
ccccatcaag cttactcgag gtcattcata tgcttgagaa gagagtcggg atagtccaaa     420
ataaaacaaa ggtaagatta cctggtcaaa agtgaaaaca tcagttaaaa ggtggtataa     480
agtaaaatat cggtaataaa aggtggccca aagtgaaatt tactcttttc tactattata     540
aaaattgagg atgttttgt cggtactttg atacgtcatt tttgtatgaa ttggttttta     600
agtttattcg cttttggaaa tgcatatctg tatttgagtc gggttttaag ttcgtttgct     660
tttgtaaata cagagggatt tgtataagaa atatctttag aaaaacccat atgctaattt     720
gacataattt ttgagaaaaa tatatattca ggcgaattct cacaatgaac aataataaga     780
ttaaaatagc tttcccccgt tgcagcgcat gggtattttt tctagtaaaa ataaaagata     840
aacttagact caaaacattt acaaaaacaa cccctaaagt tcctaaagcc caagtgcta      900 tccacgatcc atagcaagcc cagcccaacc caacccaacc cagcccaccc cagtccagcc     960
aactggacaa tagtctccac acccccccac tatcaccgtg agttgtccgc acgcaccgca    1020
cgtctcgcag ccaaaaaaaa aagaaagaa aaaaagaaa agaaaaaac agcaggtggg      1080 tccgggtcgt gggggccgga aacgcgagga ggatcgcgag ccagcgacga ggccggccct    1140
ccctccgctt ccaaagaaac gccccccatc gccactatat acatacccc cctctcctc      1200 ccatccccc aaccctacca ccaccaccac caccacctcc acctcctccc ccctcgctgc    1260
cggacgacga gctcctcccc cctcccctc cgccgccgc gcgccggtaa ccaccccgcc    1320
cctctcctct ttctttctcc gttttttttt ccgtctcggt ctcgatcttt ggccttggta    1380
gtttgggtgg gcgagaggcg gcttcgtgcg cgcccagatc ggtgcgcggg aggggcggga    1440
tctcgcggct ggggctctcg ccggcgtgga tccggcccgg atctcgcggg gaatggggct    1500
ctcggatgta gatctgcgat ccgccgttgt tgggggagat gatgggggt ttaaaatttc    1560 cgccgtgcta aacaagatca ggaagagggg aaaagggcac tatggtttat attttatat    1620 atttctgctg cttcgtcagg cttagatgtg ctagatcttt ctttcttctt tttgtgggta    1680
```

```
gaatttgaat ccctcagcat tgttcatcgg tagttttct tttcatgatt tgtgacaaat    1740
gcagcctcgt gcggagcttt tttgtaggta aagtgatca accatggcgc aagttagcag    1800
aatctgcaat ggtgtgcaga acccatctct tatctccaat ctctcgaaat ccagtcaacg    1860
caaatctccc ttatcggttt ctctgaagac gcagcagcat ccacgagctt atccgatttc    1920
gtcgtcgtgg ggattgaaga agagtgggat gacgttaatt ggctctgagc ttcgtcctct    1980
taaggtcatg tcttctgttt ccacggcgtg catgcttcac ggtgcaagca gccggcccgc    2040
aaccgcccgc aaatcctctg gcctttccgg aaccgtccgc attcccggcg acaagtcgat    2100
ctcccaccgg tccttcatgt tcggcggtct cgcgagcggt gaaacgcgca tcaccggcct    2160
tctggaaggc gaggacgtca tcaatacggg caaggccatg caggcgatgg gcgcccgcat    2220
ccgtaaggaa ggcgacacct ggatcatcga tggcgtcggc aatggcggcc tcctggcgcc    2280
tgaggcgccg ctcgatttcg gcaatgccgc cacgggctgc cgcctgacga tgggcctcgt    2340
cggggtctac gatttcgaca gcaccttcat cggcgacgcc tcgctcacaa agcgcccgat    2400
gggccgcgtg ttgaacccgc tgcgcgaaat gggcgtgcag gtgaaatcgg aagacggtga    2460
ccgtcttccc gttaccttgc gcgggccgaa gacgccgacg ccgatcacct accgcgtgcc    2520
gatggcctcc gcacaggtga agtccgccgt gctgctcgcc ggcctcaaca cgcccggcat    2580
cacgacggtc atcgagccga tcatgacgcg cgatcatacg aaaagatgc tgcagggctt    2640 tggcgccaac cttaccgtcg agacggatgc ggacggcgtg cgcaccatcc gcctggaagg    2700
ccgcggcaag ctcaccggcc aagtcatcga cgtgccgggc gacccgtcct cgacggcctt    2760
cccgctggtt gcggccctgc ttgttccggg ctccgacgtc accatcctca acgtgctgat    2820
gaaccccacc cgcaccggcc tcatcctgac gctgcaggaa atgggcgccg acatcgaagt    2880
catcaacccg cgccttgccg gcggcgaaga cgtggcggac ctgcgcgttc gctcctccac    2940
gctgaagggc gtcacggtgc cggaagaccg cgcgccttcg atgatcgacg aatatccgat    3000
tctcgctgtc gccgccgcct tcgcggaagg ggcgaccgtg atgaacggtc tggaagaact    3060
ccgcgtcaag gaaagcgacc gcctctcggc cgtcgccaat ggcctcaagc tcaatggcgt    3120
ggattgcgat gagggcgaga cgtcgctcgt cgtgcgtggc cgccctgacg gcaagggggct    3180 cggcaacgcc tcgggcgccg ccgtcgccac ccatctcgat caccgcatcg ccatgagctt    3240
cctcgtcatg ggcctcgtgt cggaaaaccc tgtcacggtg gacgatgcca cgatgatcgc    3300
cacgagcttc ccggagttca tggacctgat ggccgggctg ggcgcgaaga tcgaactctc    3360
cgatacgaag gctgcctgat gagctcgaat tcccgatcgt tcaaacattt ggcaataaag    3420
tttcttaaga ttgaatcctg ttgccggtct tgcgatgatt atcatataat ttctgttgaa    3480
ttacgttaag catgtaataa ttaacatgta atgcatgacg ttatttatga gatgggtttt    3540
tatgattaga gtcccgcaat tatacattta atacgcgata gaaaacaaaa tatagcgcgc    3600
aaactaggat aaattatcgc gcgcggtgtc atctatgtta ctagatcggg gatggggat    3660 ccactagtga tatccgtcga gtggcggccg cgttttatga ataataataa tgcatatctg    3720
tgcattacta cctgggatac aagggcttct ccgccataac aaattgagtt gcgatgctga    3780
gaacgaacgg ggaagaaagt aagcgccgcc caaaaaaaac gaacatgtac gtcggctata    3840
gcaggtgaaa gttcgtgcgc caatgaaaag gaacgatat gcgttgggta gttgggatac    3900
ttaaatttgg agagtttgtt gcatacacta atccactaaa gttgtctatc tttttaacag    3960
ctctaggcag gatataagat ttatatctaa tctgttggag ttgcttttag agtaactttt    4020
```

```
ctctctgttt cgtttatagc cgattagcac aaaattaaac taggtgacga gaaataaaga    4080
aaaacggagg cagtaaaaaa tacccaaaaa aatacttgga gattttttgtc tcaaaattat    4140 cttctaattt taaaagctac atattaaaaa tactatatat taaaaatact tcgagatcat    4200
tgcttgggat gggcagggcc aatagctaat tgctaaggat gggctatatt tatgtatcgt    4260
ctgaaacatg taggggctaa tagttagatg actaatttgc tgtgttcgta cggggtgctg    4320
tttgagccta gcgatgaagg gtcatagttt catacaagaa ctcactttg gttcgtctgc      4380 tgtgtctgtt ctcagcgtaa cggcatcaat ggatgccaaa ctccgcaagg ggacaaatga    4440
agaagcgaag agattataga acacgcacgt gtcattattt atttatggac ttgcctcagt     4500
agcttacagc atcgtacccg cacgtacata ctacagagcc acacttattg cactgcctgc    4560
cgcttacgta catagttaac acgcagagag gtatatacat acacgtccaa cgtctccact    4620
caggctcatg ctacgtacgc acgtcggtcg cgcgccaccc tctcgttgct tcctgctcgt    4680
tttggcgaat tccgatttgg caagtgttcc agagcaaaag ctggaagctc tcgtagtctg    4740
agcctctttg ctgattcata caagttatga ccatctacat ggatcgtctc accaagaaat     4800
ttgtagactg caggatttt ccctgaccgg agtgcaccag ctgggttcca actgaattta      4860
taggcaagcg gattgtttgc tgcagctgga gatggcaatc caccacagta agatgtaaat    4920
gcctttattt ttcccttcg tgcatgagct tcatcaatca tcttcattga catcaagtga      4980
tctatgccag gatctaggcc catttcacaa agtatagtta cacctgcatc tttggcagct    5040
tggctcaagt ttgacatgga ttcatcaaca tagcttgccg ttaccatgtg cttcttcaac    5100
tctatgcata ctcctgcaat ggcagcatga aaactagcag gcagcaccgg ttggacatca   5160
ttgagacagc tggaggttca tttcacttgg ttagatgtga agttggacaa agcacggatg    5220
atatgtcgta ctcagagctt gaagtaggag cagatgatac tgccacattg gataaaatta    5280
ttgattcctt gacttcttta gctaatgaac atggtggaga tcacgatgcc gggcaagaaa    5340
ttgaattagc tctgaagata ggaaaagtca atgagtatga aactgacgtc acaattgata    5400
aaggagggcc aaagatttta attcttggag ctggaagagt ctgtcggcca gctgctgagt    5460
ttctggcatc ttacccagac atatgtacct atggtgttga tgaccatgat gcagatcaaa    5520
ttcatgttat cgtggcatct ttgtatcaaa aagatgcaga agagacagtt gatggtattg    5580
aaaatacaac tgctacccag cttgatgttg ctgatattgg aagcctttca gatcttgttt    5640
ctcaggttga ggttgtaatt agcttgctgc ctgctagttt tcatgctgcc attgcaggag    5700
tatgcataga gttgaagaag cacatggtaa cggcaagcta tgttgatgaa tccatgtcaa    5760
acttgagcca agctgccaaa gatgcaggtg taactatact ttgtgaaatg ggcctagatc    5820
ctggcataga tcacttgatg tcaatgaaga tgattgatga agctcatgca cgaaagggaa    5880
aaataaaggc atttacatct tactgtggtg gattgccatc tccagctgca gcaaacaatc    5940
cgcttgccta taaattcagt tggaacccag ctggtgcact ccggtcaggg aaaaatcctg    6000
cagtctacaa atttcttggt gagacgatcc atgtagatgg tcataacttg tatgaatcag    6060
caaagaggct cagactacga gagcttccag cttttgctct ggaacacttg ccaaatcggg    6120
atccgcagct gcacgggtcc aggaaagcaa tcgcatagtc aagctaaatc atcaagatgc    6180
aaacttttcg ccccttgctaa acacggtaaa attcgaatgg acatgtgtgg agcagcaaag    6240
gccttacgtc cgagaaacag ggccactcaa cgagttagtt aaattcaaag aaagaaacgc    6300
ctccttgcaa gttgcaacat tcttagatca tactgatgaa aatgacgtct ttcattaaag    6360
aacagggaag atagatcttt gctcaatatc gtatgatgtg ttcagccaga ctgtcggatg    6420
```

```
gaccacacgg taatagcagt gctggacgat gttacatcga gaaagattac tagccttttc    6480
atgggagtga aggatataaa agaaataagt tcaccacgat tgcaggatag catacaagat    6540
cagcgccact gcggcactgt tcatcgaaaa aaaaactgtg gacgaagcta gctttcccca    6600
aaattactca acgaatcata aaccaagatt agtcagatca agagacagag gagaaacaag    6660
gcggaccttt gcacttgatc ggatccttgg gttggctgta tgcagaacta agcggaggt    6720 ggcgcgcatt tataccagcg ccgggccctg gtacgtggcg cggccgcgcg gctacgtgga    6780
ggaaggctgc gtggcagcag acacacgggt cgccacgtcc cgccgtactc tccttaccgt    6840
gcttatccgg gctccggctc ggtgcacgcc agggtgtggc cgcctctgag cagactttgt    6900
cgtgttccac agtggtgtcg tgttccgggg actccgatcc gcggcgagcg accgagcgtg    6960
taaaagagtt cctactaggt acgttcattg tatctggacg acgggcagcg gacaatttgc    7020
tgtaagagag gggcagtttt ttttagaaa acagagaat tccgttgagc taattgtaat      7080
tcaacaaata agctattagt tggttttagc ttagattaaa gaagctaacg actaatagct    7140
aataattagt tggtctatta gttgactcat tttaaggccc tgtttcaatc tcgcgagata    7200
aactttagca gctattttt agctactttt agccatttgt aatctaaaca ggagagctaa     7260
tggtggtaat tgaaactaaa ctttagcact tcaattcata tagctaaagt ttagcaggaa    7320
gctaaacttt atcccgtgag attgaaacgg ggcctaaatc tctcagctat ttttgatgca    7380
aattactgtc actactggaa tcgagcgctt tgccgagtgt caaagcctga aaaacactcc    7440
gtaaagactt tgcctagtgt gacactcgac aaagagatct cgacgaacag tacatcgaca    7500
acggcttctt tgtcgagtac tttttatcgg acacttgaca aagtctttgt cgagtgaact    7560
acattgaaac tctatgattt tatgtgtagg tcacttaggt ttctacacat agtacgtcac    7620
aactttaccg aaacattatc aaattttat cacaacctct atatatgata tcatgacatg     7680
tggacaagtt tcattaattt ctgactttat ttgtgtttta tacaattttt aaacaactag    7740
ataacaagtt cacggtcatg tttagtgagc atggtgcttg aagattctgg tctgcttctg    7800
aaatcggtcg taacttgtgc tagataacat gcatatcatt tatttgcat gcacggtttt     7860 ccatgtttcg agtgacttgc agtttaaatg tgaattttcc gaagaaattc aaataaacga    7920
actaaatcta atatttatag aaaacatttt tgtaaatatg taattgtgcc aaaatggtac    7980
atgtagatct acatagtgta ggaacatacc acaaaaagtt tggttggcaa ataaaaaaa     8040 ataaaatata ctttatccga gtgtccaagg tatggcactc ggcccgggtg gccaagctta    8100
ctagcccggg cgcgccttaa ttaagcggcc gcatcgatcg tgaagtttct catctaagcc    8160
cccatttgga cgtgaatgta gacacgtcga aataaagatt tccgaattag aataatttgt    8220
ttattgcttt cgcctataaa tacgacggat cgtaatttgt cgttttatca aaatgtactt    8280
tcattttata ataacgctgc ggacatctac attttgaat tgaaaaaaa ttggtaatta      8340 ctctttcttt ttctccatat tgaccatcat actcattgct gatccatgta gatttccgg     8400 acatgaagcc atttacaatt gaatatatcc tgccgccgct gccgctttgc acccggtgga    8460
gcttgcatgt tggtttctac gcagaactga gccggttagg cagataattt ccattgagaa    8520
ctgagccatg tgcaccttcc ccccaacacg gtgagcgacg gggcaacgga gtgatccaca    8580
tgggactttt                                                            8590
```

<210> SEQ ID NO 2
<211> LENGTH: 7794
<212> TYPE: DNA

<213> ORGANISM: Artificial
<220> FEATURE:
<223> OTHER INFORMATION: Recombinant construct

<400> SEQUENCE: 2

```
aggattttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc    180
actcccgagg ggaaccctgt ggttggcatg cacatacaaa tggacgaacg gataaacctt    240
ttcacgccct tttaaatatc cgattattct aataaacgct cttttctctt aggtttaccc    300
gccaatatat cctgtcaaac actgatagtt taaactgaag gcgggaaacg acaatctgat    360
ccccatcaag cttactcgag gtcattcata tgcttgagaa gagagtcggg atagtccaaa    420
ataaaacaaa ggtaagatta cctggtcaaa agtgaaaaca tcagttaaaa ggtggtataa    480
agtaaaatat cggtaataaa aggtggccca aagtgaaatt tactcttttc tactattata    540
aaaattgagg atgttttgt cggtactttg atacgtcatt tttgtatgaa ttggttttta     600
agtttattcg cttttggaaa tgcatatctg tatttgagtc gggttttaag ttcgtttgct    660
tttgtaaata cagagggatt tgtataagaa atatctttag aaaaacccat atgctaattt    720
gacataattt ttgagaaaaa tatatattca ggcgaattct cacaatgaac aataataaga    780
ttaaaatagc tttcccccgt tgcagcgcat gggtatttt tctagtaaaa ataaagata      840
aacttagact caaaacattt acaaaaacaa cccctaaagt tcctaaagcc caaagtgcta    900
tccacgatcc atagcaagcc cagcccaacc caacccaacc caacccaccc cagtccagcc    960
aactggacaa tagtctccac acccccccac tatcaccgtg agttgtccgc acgcaccgca   1020
cgtctcgcag ccaaaaaaaa aagaaagaa aaaaagaaa aagaaaaaac agcaggtggg     1080
tccgggtcgt gggggccgga aacgcgagga ggatcgcgag ccagcgacga ggccggccct   1140
ccctccgctt ccaaagaaac gccccccatc gccactatat acatacccc cctctcctc    1200
ccatcccccc aaccctacca ccaccaccac caccacctcc acctcctccc cctcgctgc    1260
cggacgacga gctcctcccc cctcccctc cgccgccgcc gcgccggtaa ccaccccgcc   1320
cctctcctct ttctttctcc gtttttttt ccgtctcggt ctcgatcttt ggccttggta    1380
gtttgggtgg gcgagaggcg gcttcgtgcg cgcccagatc ggtgcgcggg aggggcggga   1440
tctcgcggct ggggctctcg ccggcgtgga tccggcccgg atctcgcggg gaatggggct   1500
ctcggatgta gatctgcgat ccgccgttgt tgggggagat gatggggggt ttaaaatttc   1560
cgccgtgcta aacaagatca ggaagagggg aaaagggcac tatggtttat attttatat    1620
attctgctg cttcgtcagg cttagatgtg ctagatcttt cttctcttctt tttgtgggta   1680
gaatttgaat ccctcagcat tgttcatcgg tagttttct tttcatgatt tgtgacaaat    1740
gcagcctcgt gcggagcttt tttgtaggta gaagtgatca accatggcgc aagttagcag   1800
aatctgcaat ggtgtgcaga acccatctct tatctccaat ctctcgaaat ccagtcaacg   1860
caaatctccc ttatcggttt ctctgaagac gcagcagcat ccacgagctt atccgatttc   1920
gtcgtcgtgg ggattgaaga agagtgggat gacgttaatt ggctctgagc ttcgtcctct   1980
taaggtcatg tcttctgttt ccacggcgtg catgcttcac ggtgcaagca gccggcccgc   2040
aaccgcccgc aaatcctctg gccttttccgg aaccgtccgc attcccggcg acaagtcgat   2100
ctcccaccgg tccttcatgt tcggcggtct cgcgagcggt gaaacgcgca tcaccggcct   2160
tctggaaggc gaggacgtca tcaatacggg caaggccatg caggcgatgg gcgcccgcat   2220
```

```
ccgtaaggaa ggcgacacct ggatcatcga tggcgtcggc aatggcggcc tcctggcgcc    2280
tgaggcgccg ctcgatttcg gcaatgccgc cacgggctgc cgcctgacga tgggcctcgt    2340
cggggtctac gatttcgaca gcaccttcat cggcgacgcc tcgctcacaa agcgcccgat    2400
gggccgcgtg ttgaacccgc tgcgcgaaat gggcgtgcag gtgaaatcgg aagacggtga    2460
ccgtcttccc gttaccttgc gcgggccgaa gacgccgacg ccgatcacct accgcgtgcc    2520
gatggcctcc gcacaggtga agtccgccgt gctgctcgcc ggcctcaaca cgcccggcat    2580
cacgacggtc atcgagccga tcatgacgcg cgatcatacg gaaaagatgc tgcagggctt    2640
tggcgccaac cttaccgtcg agacggatgc ggacggcgtg cgcaccatcc gcctggaagg    2700
ccgcggcaag ctcaccggcc aagtcatcga cgtgccgggc gacccgtcct cgacggcctt    2760
cccgctggtt gcggccctgc ttgttccggg ctccgacgtc accatcctca acgtgctgat    2820
gaaccccacc cgcaccggcc tcatcctgac gctgcaggaa atgggcgccg acatcgaagt    2880
catcaacccg cgccttgccg gcggcgaaga cgtggcggac ctgcgcgttc gctcctccac    2940
gctgaagggc gtcacggtgc cggaagaccg cgcgccttcg atgatcgacg aatatccgat    3000
tctcgctgtc gccgccgcct cgcggaagg ggcgaccgtg atgaacggtc tggaagaact    3060
ccgcgtcaag gaaagcgacc gcctctcggc cgtcgccaat ggcctcaagc tcaatggcgt    3120
ggattgcgat gagggcgaga cgtcgctcgt cgtgcgtggc cgccctgacg gcaaggggct    3180
cggcaacgcc tcgggcgccg ccgtcgccac ccatctcgat caccgcatcg ccatgagctt    3240
cctcgtcatg ggcctcgtgt cggaaaaccc tgtcacggtg gacgatgcca cgatgatcgc    3300
cacgagcttc ccggagttca tggacctgat ggccgggctg ggcgcgaaga tcgaactctc    3360
cgatacgaag gctgcctgat gagctcgaat tcccgatcgt tcaaacattt ggcaataaag    3420
tttcttaaga ttgaatcctg ttgccggtct tgcgatgatt atcatataat ttctgttgaa    3480
ttacgttaag catgtaataa ttaacatgta atgcatgacg ttatttatga gatgggtttt    3540
tatgattaga gtcccgcaat tatacattta atacgcgata gaaaacaaaa tatagcgcgc    3600
aaactaggat aaattatcgc gcgcggtgtc atctatgtta ctagatcggg gatgggggat    3660
ccactagtga tatccgtcga ctggtaccta cgcgtagcta gcccgggcgc gccttaatta    3720
agcggccgct tcgagtggct gcaggtcgat tgatgcatgt tgtcaatcaa ttggcaagtc    3780
ataaaatgca ttaaaaaata ttttcatact caactacaaa tccatgagta aactataat    3840 tataaagcaa tgattagaat ctgacaagga ttctggaaaa ttacataaag gaaagttcat    3900
aaatgtctaa aacacaagag gacatacttg tattcagtaa catttgcagc ttttctaggt    3960
ctgaaaatat atttgttgcc tagtgaataa gcataatggt acaactacaa gtgttttact    4020
cctcatatta acttcggtca ttagaggcca cgatttgaca cattttttact caaaacaaaa    4080 tgtttgcata tctcttataa tttcaaattc aacacacaac aaataagaga aaaacaaat    4140 aatattaatt tgagaatgaa caaaaggacc atatcattca ttaactcttc tccatccatt    4200
tccatttcac agttcgatag cgaaaaccga ataaaaaaca cagtaaatta caagcacaac    4260
aaatggtaca agaaaaacag ttttcccaat gccataatac tcaaactcag taggattctg    4320
gtgtgtgcgc aatgaaactg atgcattgaa cttgacgaac gttgtcgaaa ccgatgatac    4380
gaacgaaagc tgaattccta gctggctgaa tggtagtagt tgttgctgct gtaaataagc    4440
aggagagttc aatgctgtca gttggttgaa tggaagaaat tgctgggggt aggcagcaga    4500
tagctggctg aatggtagtt gttgttgttg caaataagaa gcagagttca atgcagctag    4560
```

```
ttggttgaat ggaagaaact gctgttgctg agagtaggca gcaaggtttg ctagcacaag      4620
ttgttgtagt tgttgtgccc tgatgttttg tgccaataaa tgcaccaaag gtaactgctg      4680
taatagggct gatgattgtt ggaggaacaa gggtgataaa ggtaagatgc cagctgcgat      4740
tgcctgttat gcataaagat ggcacctcca acgatgggtt gctgcaaggc agggttcatc      4800
aaagagaact ggttgtatgg cagcaattgt tgttgctgct gcaggaaggt agcgaccaat      4860
gggttagcca ctgccaatgg attaagtaac tgttgtcgct gttgtaggta cgcagcagag      4920
tttgacacag ccagttggtt gaatggaagc aactgttgta agtaggcagc agggtttgcc      4980
acagctagct gagtcagagc tggtacaatt tgttgcagca actgttgttg taggtacgta      5040
ggtgggcccg ctaccaagat attagccctc cttgcgcttc ttgccctttt agtgagcgca      5100
acaaatgcgt tcattattcc acagtgctca cttgctccta gtgccagtat tccacagttc      5160
ctcccaccag ttacttcaat gggcttcgaa catccagccg tgcaagccta caggctacaa      5220
ctagcgcttg cggcgagcgc cttacaacaa ccaattgccc aattgcaaca acaatccttg      5280
gcacatctaa ccctacaaac cattgcaacg caacaacaac aacaacagtt tctgccatca      5340
ctgagccacc tagccgtggt gaaccctgtc acctacttgc aacagcagct gcttgcatcc      5400
aacccacttg ctctggcgaa cgtagctgca taccagcaac aacaacagct gcaacagttt      5460
atgccagtgc tcagtcaact agccatggtg aaccctgccg tctacctaca actactttca      5520
tctagcccgc tcgcggtggg caatgcacct acgtacctac aacaacagtt gctgcaacaa      5580
attgtaccag ctctgactca gctagctgtg gcaaaccctg ctgcctactt acaacagttg      5640
cttccattca accaactggc tgtgtcaaac tctgctgcgt acctacaaca gcgacaacag      5700
ttacttaatc cattggcagt ggctaaccca ttggtcgcta ccttcctgca gcagcaacaa      5760
caattgctgc catacaacca gttctctttg atgaaccctg ccttgcagca acccatcgtt      5820
ggaggtgcca tctttaccgg taacaggcaa tcgcagctgg catcttacct ttatcaccct      5880
tgttcctcca acaatcatca gcccctattac agcagttacc tttggtgcat ttattggcac      5940
aaaacatcag ggcacaacaa ctacaacaac ttgtgctagc aaaaccttgct gcctactctc      6000 agcaacaaca gtttcttcca ttcaaccaac tagctgcatt gaactctgct tcttatttgc      6060
aacaacaaca actaccattc agccagctat ctgctgccta ccccccagcaa tttcttccat      6120 tcaaccaact gacagctttg aactctcctg cttatttaca gcagcaacaa ctactaccat      6180
tcagccagct agggatccgg taccgggttc ttctgcgctc tggagtagat aaagctaatg      6240
gtctgaagac ccagtggtgg tgatggagaa gtgcacaggc atgcgagcgt tatttatagc      6300
tttgattaat taacacaatt tcttgtgttc ttatgccacc gagacggctg taggcagctt      6360
catggtttct tgccaaatgt atatgactcg tcactctctt tacgtagcac gtcgatggtt      6420
catctggaat cattctgtac ttctgcgtgg ctcagttttg ttgccttcta caggttgttg      6480
atctacgtaa aacgaattag atttagcttg acatatggct tttttttttgt tgtaaattta      6540 ctttacacgt caaggatttt tgtcctgtcc ggcctatttt attttcatg aaacgatctt       6600 tgtaatgcaa tatgagttgt ttgtaatgtc ttgtgagctg taagcatgta tatcagatga      6660
gtatgatctc ggcatgactc accgtgtttc tttgcacaca gagaggattt gtttgattgt      6720
ttcttaccca ataccttga cgtgcaattt tggttgatgt tctgtgagtt gttaaggata       6780
caacaaattc ttggagcttt acatgccaat gcatggttgt ttcgtgttcc tcaccacttt      6840
aggacttata cggttgcacc tggatgatcg aaggggattg ggagagatta aatctccttc      6900
tattcaattt tgactaggaa gagatttaat cgtttccaac cccttttcgat ccagacgtaa     6960
```

```
gcgaacaagt tttttatttg gatacoctct tattcatctt aatacacaca tgtattaagt    7020
tgcactagtt atatgccogt gcattgctac ggtttatata tatatatata tatatgtata    7080
tatatatata tgatatatga taaattttgt tttaataaaa catatgtttt ctattgatta    7140
ggttgtgtga atatggagcc aacaaccaat atccagaaca cttatacata atttcacctt    7200
attttgtaca taaactctct tattatagta gtagagaaga gattataaga gtgcgggttg    7260
attataaaga aatgtaggag ttttttaata atattgacgc gggacaagct tactagtagc    7320
ttgttaacgc ggccgcatcg atcgtgaagt ttctcatcta agcccccatt tggacgtgaa    7380
tgtagacacg tcgaaataaa gatttccgaa ttagaataat ttgtttattg ctttcgccta    7440
taaatacgac ggatcgtaat ttgtcgtttt atcaaaatgt actttcattt tataataacg    7500
ctgcggacat ctcattttt gaattgaaaa aaaattggta attactcttt cttttctcc      7560 atattgacca tcatactcat tgctgatcca tgtagatttc ccggacatga agccatttac    7620
aattgaatat atcctgccgc cgctgccgct ttgcaccogg tggagcttgc atgttggttt    7680
ctacgcagaa ctgagccggt taggcagata atttccattg agaactgagc catgtgcacc    7740 ttcccccaa cacggtgagc gacggggcaa cggagtgatc cacatgggac tttt           7794
```